United States Patent
Munoz et al.

(10) Patent No.: US 6,617,426 B1
(45) Date of Patent: Sep. 9, 2003

(54) CYSTEINYL PROTEASE INHIBITORS

(76) Inventors: Benito Munoz, 10741 Frank Daniels Rd., San Diego, CA (US) 92131; Kuman Srinivasan, 7693 Palmilla Dr., Apt. #2116, San Diego, CA (US) 92122; Bowei Wang, 7825 Roan Rd., San Diego, CA (US) 92129

( * ) Notice: Subject to any disclaimer, the term of this patent is extended or adjusted under 35 U.S.C. 154(b) by 0 days.

(21) Appl. No.: 09/338,409

(22) Filed: Jun. 22, 1999

(51) Int. Cl.$^7$ .................................................. C07K 5/08
(52) U.S. Cl. ........................... 530/331; 514/18; 514/19
(58) Field of Search ........................ 530/331; 514/18, 514/19

(56) References Cited

U.S. PATENT DOCUMENTS 5,856,530 A * 1/1999 Webber ....................... 549/478

OTHER PUBLICATIONS

T.E. Golde et al., Science, 255:728–730(1992).
M. Citron et al., Neuron, 17:171–179(1996).
H.–W. Klafki et al., J. Biol. Chem., 271:28655–28659(1996).
R. Siman et al., J. Biol. Chem., 268;16602–16609(1993).
J. Busciglio et al., Proc. Natl. Academy of Science, U.S.A., 90:2092–2096(1993).
C. Haass et al., J. Biol. Chem. 268:3021–3024(1993).
H.–W. Klafki et al., Neuroscience Lett. 201:29–32(1995).

* cited by examiner

Primary Examiner—Christopher S. F. Low
Assistant Examiner—David Lukton
(74) Attorney, Agent, or Firm—David Rubin; Curtis C. Panzer; David L. Rose

(57) ABSTRACT

Amino acid di- and tri-peptide analogs having C-terminal vinylic groups, pharmaceutical compositions containing the analogs and methods of treating diseases using cysteinyl protease inhibitors; particularly neurodegenerative, autoimmune, cognitive disorders, stroke and traumatic injury.

19 Claims, No Drawings

CYSTEINYL PROTEASE INHIBITORS

FIELD OF THE INVENTION

The invention relates to protease inhibitor compounds useful in treatments of neurodegenerative, cardiovascular, pulmonary, neuromuscular, musculovascular and autoimmune diseases characterized by tissue damage, induction of apoptosis, cell death and/or the accumulation of amyloid proteins in deposits, plaques, fibrils and tangles.

BACKGROUND OF INVENTION

Cysteinyl proteases are implicated in important cellular processes including endocytosis and degradation of proteins, immune recognition, apoptosis and processing of amyloid precursor protein. Cysteinyl proteases are localized in the endosomal lysosomal compartment, possibly the endoplasmic reticulum and cytosol. While many of the molecular details are at present uncertain, the importance of cysteinyl proteases at the cellular level and at an organism level cannot be overstated.

In Alzheimer's disease (AD), amyloid precursor protein (APP; i.e., $APP_{695}$) is proteolytically processed in neural cells and Aβ cleavage fragments are secreted into cerebral extracellular perivascular matix. Plaques containing Aβ act as a pathological landmark of AD (2–5) and in vitro studies have shown to that Aβ can aggregate into insoluble fibrils which ultrastructurally resemble amyloid plaques (7). Aggregated in a fibrillar beta-pleated sheet configuration, Aβ is thought to form a nidus for binding other proteins contributing to Alzheimer's dementia and pathology. Aβ fibrils are reportedly toxic for cultured neurons in vitro (8), possibly through induction of apoptosis (9), initiation of free radical formation (10) or increases in peroxide ($H_2O_2$) levels in cells (11).

APP, synthesized by neuronal cells, full length APP may be degraded in lysosomes (21,22), resulting in non-amyloidogenic fragments, or it can be proteolytically processed to polypeptides of 110 kDa, i.e., sAPP (16–17); 9–10 kDa (17); and 4.2 kDa, i.e., Aβ (18–19). Characterization of fragments and protease inhibitor profiles suggest three intracellular enzymes, termed secretases, differing as follows: namely, Alpha-secretase (α-secretase) mediates cleavage of $APP_{695}$ and $APP_{751}$ producing sAPP (110 kDa) and a 9–10 kDa carboxy-terminal-fragment (CTF; i.e., $APP_{611-695}$). The CTF fragment may undergo further degradation in lysosomes (17). Products of lysosomal and α-secretase cleavages are generally considered to be non-amyloidogenic;

Beta-secretase (β-secretase) mediates cleavage of $APP_{695}$ in the carboxy-terminal region (i.e., at APP $Met_{595}$-$Asp_{596}$; Aβ $Asp_1$; 23), producing a 11.4–11.8 kDa fragment, 100 amino acids in length (CTF100), and containing the Aβ domain; and, Gamma-secretase (γ-secretase) mediates cleavage in the C-terminal transmembrane domain of APP, and possibly also CTF100, to release the $Aβ_{1-39}$, $Aβ_{1-40}$ and/or $Aβ_{1-42}$ peptides. Both $Aβ_{1-40}$ and $Aβ_{1-42}$ are reportedly amyloidogenic; with $Aβ_{1-42}$ being more active than $Aβ_{1-40}$ (7,24,25).

Sensitivity of secretases to protease inhibitors has been studied in cell-based assays, i.e., by treating APP producer cells with protease inhibitors. Results have varied in different cells and under differing conditions of culture. In certain reports, APP cleavage is reportedly inhibited by serine protease inhibitors; in others by inhibitors of chymotrypsin-like enzymes; and in others by inhibitors of cysteinyl proteases such as cathepsins B, D, H, L and S and calpain. Studies with leupeptin (26,27), E64 and Z-Phe-Ala-$CHN_2$ (28), i.e., lysosomal enzyme inhibitors, have failed to implicate known lysosomal hydrolases in production of Aβ. Similarly, although calpain inhibitor I, a caspase inhibitor, was initially reported effective in reducing Aβ levels in vitro (29), subsequent findings seem at odds with an effect on a putative γ-secretase (30). Dipeptidyl-aldehyde inhibitor, Z-L-Val-L/D-Phe-aldehyde (MDL 28170) and AEBSF [4-(2-aminoethyl)-benzenesulfonyl fluoride hydrochloride] were also once thought to inhibit $Aβ_{1-42}$ production (32). Since non-specific acidotropic agents such as $NH_4Cl$ and chloroquine, or Golgi inhibitors such as brefeldin A and monensin (19,27), reportedly affect APP processing it is possible that it takes place in the endoplasmic reticulum (ER) and/or Golgi apparatus. Specific and targeted inhibitors of secretase enzymes have (to date) proven elusive.

In apoptosis, an intracellular cascade of cysteinyl proteases, termed caspases, is activated by radiation damage to cellular DNA or structures (e.g., mitochondria), or by removal of one or more critical growth factors (e.g., EGF, PGF, TGFβ, NGF, BDNF), glucose or serum. In addition, a variety of different receptor ligand interactions at the cell surface may trigger apoptosis in vitro: e.g., anti-Fas antibody or Fas ligand binding to Fas receptor; IL-1 binding to IL-1Rβ; TNFα binding to TNFR1 and TNFR2; Apo 3 ligand binding to Death Receptor 3; glucocorticoids binding to cell surface glycocorticoid receptors; TRAIL, TRANCE and NOC18 binding to yet other cell surface "death" receptors. Important cysteinyl proteases activated in this manner are thought to include caspases 3, 8 and 9.

Apoptosis has recently been implicated in mechanisms by which tissue damage is triggered following traumatic injury, vascular insufficiency and stroke.

Using knockout mice, Cathepsin S is reportedly involved in class I MHC antigen processing, i.e., of self and viral antigens, while Cathepsin L is involved in class II processing of foreign proteins.

Thus, protease inhibitors find a variety of important medical and veterinary uses in treatments of diseases, as well as, uses in the food, dairy, agriculture, chemical and biotechnology industries.

SUMMARY OF THE INVENTION

Cysteinyl protease inhibitors, pharmaceutical compositions and methods of treating protein processing disorders, trauma, stroke, autoimmunity, neurodegenerative and cognitive disorders including Alzheimer's disease, are disclosed. The di- and tri-peptide analogues with unnatural α-amino side chain residues and derivatized amino and carboxyl terminal residues constitute highly effective inhibitors of cysteinyl proteases including e.g. cathepsins, caspases, calpains and secretases. Methods and pharmaceutical compositions are provided for modulating activities of cysteinyl proteases involved in diseases including methods for altering secretase-mediated processing of APP in Alzheimer's disease and aberrant cathepsin S-mediated processing of self proteins for MHC class I presentation in autoimmune diseases. The instant compounds include vinyl sulfides, sulfoxides, sulfones, amines, amine oxides, phosphines, phosphine oxides, phosphinates and phosphonates of peptidyl analogs of di- and tri-peptides, where the vinyl substituent in the peptidyl analog preferably occupies the carboxyl-terminal position and consists of a substituted alkenyl or alkynyl side chain.

DETAILED DESCRIPTION OF THE PREFERRED EMBODIMENTS

Embodiments of the invention provide cysteinyl protease inhibitors. The instant compounds are vinyl heterocyclic alkyls and aryl adducts of peptidyl analogs of natural α-amino acid containing cysteinyl protease substrates; according to the following FORMULA I, II or III: namely,

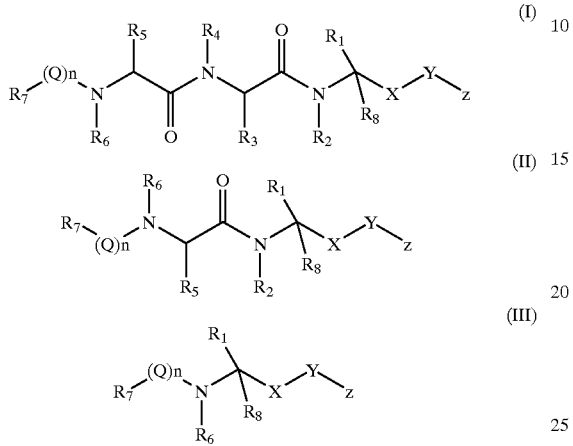

wherein $R_1$ is an unnatural amino acid side chain, preferably a lower alkenyl or lower alkynyl that is unsubstituted, or alternatively, substituted with W, W, in turn, is halo, hydroxy, alkyl, aryl, heterocycle, heteroaryl, alkoxy, aminosulfonyl, alkylcarbonyl, arylcarbonyl, heteroarylcarbonyl, heterocyclecarbonyl, nitro, haloalkyl; preferably, trifluoromethyl, cyano, amino or aminocarbonyl; and most preferably, a side chain not present in a natural amino acid;

X is —CH=CH—(CH=CH)$_k$—(CH$_2$)$_j$ or —CH$_2$CH$_2$—(CH$_2$)$_b$ where "k" is 0–9, preferably 0–3, and most preferably 0; "j" is 0–4, preferably 0–2, most preferably 0; and, "b" is 0–6, preferably 3–6, most preferably 3 or 4;

Y is S, SO, SO$_2$, NR$_{20}$O, —N(O)(R$_{20}$)—, —PR$_{20}$, —P(O)(R$_{20}$)—, —P(O)O— or —P(O)(OR$_{20}$)O—; wherein, $R_{20}$ is hydrogen, alkyl or aryl;

Z is —(CH$_2$)$_i$—A; "i" is 0–4, preferably 0–2, most preferably 0; wherein, A is a substituted or unsubstituted heterocycle, heteroaryl or aryl; where the substituents consist of one or more L groups; wherein, L is halogen, lower alkyl, lower alkenyl, lower alkynyl, alkoxy, aryloxy, hydroxy, haloalkyl, preferably trifluoromethyl, nitro, nitrile, alkylthio, phenyl, and —NR$_{30}$R$_{31}$; and, in optional embodiments L may be further substituted with W, as set forth above, but preferably L is selected from the substituents set forth in regard to V, below;

$R_{30}$ and $R_{31}$ are each independently H, alkyl, preferably lower alkyl, hydroxy or halo lower alkyl, and most preferably trifluoromethyl;

V is OH, halogen, lower alkyl, preferably methyl or ethyl or halogen-substituted lower alkyl, preferably halogen-substituted methyl or ethyl, and is more preferably OH;

$R_2$, $R_3$, $R_4$, $R_5$, $R_6$, $R_7$, $R_8$, Q and n are each selected from (i), (ii), (iii), (iv), (v), (vi) and (vii) as follows;

(i) $R_3$ and $R_5$ are each independently selected from a side chain of a naturally occurring α-amino acid; H; alkyl, preferably lower (C$_{1-6}$) alkyl; alkenyl, preferably C$_{2-10}$ alkenyl; alkynyl, preferably C$_{2-6}$ alkynyl; aryl, aralkyl, aralkenyl, aralkynyl; heteroaryl, heteroaralkyl, heteroaralkenyl, heteroaralkynyl; L-substituted aryl, L-substituted aralkyl, L-substituted aralkenyl, L-substituted aralkynyl; M-substituted heteroaryl, M-substituted heteroaralkyl, M-substituted heteroaralkenyl and M-substituted heteroaralkynyl; wherein, M is lower alkyl, preferably C$_{1-4}$ alkyl, or alternatively, M is halo-lower alkyl, preferably C$_{1-4}$ haloalkyl, but most preferably M is trifluoromethyl;

$R_2$, $R_4$, $R_6$, and $R_8$ are each independently selected from among H; lower alkyl, preferably C$_{1-4}$ alkyl; cycloalkyl, preferably lower cycloalkyl; and cycloalkylalkyl, preferably lower cycloalkylalkyl;

$R_7$ is selected from among C$_{1-6}$ alkyl; R$_A$R$_B$CH; L-substituted or unsubstituted aryl; alkenyl; alkynyl; 9-fluorenyl; aralkyl; aralkenyl; aralkynyl; L-substituted or unsubstituted monocylic or bicyclic heterocycle; L-substituted or unsubstituted monocyclic or bicyclic aryl, L-substituted or unsubstituted bicyclic aryl-heteroaryl, and L-substituted or unsubstituted monocyclic or bicyclic heteroaryl;

Q is —C(O)—, —O—C(O)—, —S(O)$_2$— or —HN—C(O)—;

n is zero or one;

$R_A$ is —(T)$_m$, —(D)$_m$, —R$_3$, wherein T is O or NH, D is C$_{1-4}$ alkyl or C$_{2-4}$ alkenyl and m is zero or one; and $R_B$ is selected in the same manner as in regard to $R_3$ and $R_5$, above; or (ii) $R_2$, $R_5$ and $R_8$ are selected as in (i), above;

$R_3$ and $R_4$ are selected as in either of (i), above, or (iv), below;

n is zero; and $R_6$ and $R_7$ together with the atoms to which each is attached form a 3–10 membered ring, preferably a 4–8 membered ring, most preferably a substituted or unsubstituted 5–6 membered heterocyclic moiety containing 1–5 heteroatoms, where the substituents of the ring are selected either from those identified in regard to L, above, but, preferably those identified in regard to V, above, and most preferably the substituents so chosen will, together with the ring members will form a morpholino, thiomorpholino, pyrrolidinyl, V-substituted pyrrolidinyl, or 4-hydroxypyrrolidinyl ring; or (iii) $R_2$, $R_3$, $R_4$, $R_5$ and $R_8$ are selected as set forth in regard to (i), above;

Q is —C(O)— n is one; and $R_6$ and $R_7$ are substituted or unsubstituted carbonyl (—(C=O)—), phenyl, a heteroatom, lower alkylene, preferably C$_{2-3}$ alkylene, or lower alkylene linked to a heteroatom, preferably C$_{2-3}$ alkylene linked to a heteroatom; together with the atoms to which they are attached $R_6$ and $R_7$ form a cyclic moiety, preferably a 4–6 membered cyclic or 8–12 membered bicyclic moiety, most preferably the subject moiety is succinimidyl, phthalimidyl or maleimidyl; and, wherein the substituents are selected from those set forth in regard to L, above, but preferably those set forth in regard to V, above, and (iv) $R_2$, $R_5$, $R_6$, $R_7$, $R_8$, Q and n are selected as set forth above in regard to any of (i)–(iii), above, or (v)–(vii), below;

$R_3$ and $R_4$ are substituted or unsubstituted lower alkylene, preferably $C_{1-4}$ alkylene, or lower alkylene linked to a heteroatom, preferably $C_{2-4}$ alkylene linked to a heteroatom, or a heteroatom; together with the atoms to which they are attached, $R_3$ and $R_4$ form a heterocyclic moiety, preferably a 4–6 membered heterocyclic moiety, most preferably morpholino, thiomorpholino, pyrrolidinyl, or V-substituted pyrrolidinyl, particularly 4-hydroxypyrrolidinyl; wherein, the substituents of $R_3$ and/or $R_4$ are selected from those set forth in regard to L, above, but preferably to those set forth in regard to V, above; or (v) $R_2$, $R_7$, $R_8$, Q and n are selected as set forth in regard to (i), above;

$R_3$ and $R_4$ are selected as in either of (i) or (iv), above;

$R_5$ and $R_6$ are each independently substituted or unsubstituted lower alkylene, preferably $C_{2-4}$ alkylene, or lower alkylene linked to a heteroatom, preferably $C_{2-4}$ alkylene linked to a heteroatom, or a heteroatom; together with the atoms to which they are attached $R_5$ and $R_6$ form a heterocyclic moiety, preferably a 4–6 membered heterocyclic moiety, most preferably a moiety selected from among morpholino, thiomorpholino, pyrrolidinyl, or V-substituted pyrrolidinyl, particularly 4-hydroxypyrrolidinyl; wherein, the substituents of $R_5$ and/or $R_6$ are selected from those set forth in regard to L, above, but preferably to those set forth in regard to V, above; or (vi) $R_2$, $R_6$ and $R_8$ are selected as set forth in regard to (i), above;

$R_3$ and $R_4$ are selected as in either of (i) or (iv), above; n is zero; and $R_5$ and $R_7$ are substituted or unsubstituted lower alkylene, preferably $C_{2-4}$ alkylene, or lower alkylene linked to a heteroatom, preferably $C_{2-4}$ alkylene linked to a heteroatom, or a heteroatom; together with the atoms to which they are attached $R_5$ and $R_7$ form a heterocyclic moiety, preferably a 4–6 membered heterocyclic moiety, most preferably selected from among morpholino, thiomorpholino, pyrrolidinyl, or V-substituted pyrroliclinyl, particularly 4-hydroxypyrrolidinyl; wherein, the substituents of $R_5$ and/or $R_7$ are selected from those set forth in regard to L, above, but preferably to those set forth in regard to V, above; or (vii) $R_2$, $R_5$ and $R_8$ are selected as set forth in regard to (i), above;

$R_3$ and $R_4$ are selected as in either of (i) or (iv), above; n is 0;

$R_6$ and $R_7$ together with the atoms to which each is attached form a 6–12, preferably an 8–10 membered bicyclic heterocyclic or heteroaryl moiety, preferably a reduced isoquinolinyl moiety, more preferably a 1,2,3,4-tetrahydroisoquinolinyl moiety;

and in all of (i)–(vii), above, unless specified otherwise: (a) the carbon chains, where so indicated, are straight or branched chain containing from 1 to about 12 carbons preferably 1 to about 6, and most preferably 4 to about 6 carbons; and (b) the cyclic moieties, where so indicated, contain one ring or two fused rings, each ring, or combination of rings, preferably containing 3 to about 16 atoms, most preferably 4 to about 12 atoms, and in a combination of two fused rings most preferably each of the subject rings contains 4 to about 6 ring atoms.

Abbreviations used are e.g., AD, Alzheimer's disease; Aβ, Aβ-amyloid peptide; APP, amyloid precursor protein; $APP_{751}$, wild-type human APP-751 protein; $APP_{695WT}$, wild-type human APP-695 protein; $APP_{670/671}$, human APP-695 protein harboring the "Swedish" double mutation at codons 670 and 671; $APP_{670/671/717}$, human APP-770 protein containing the "Swedish" double mutation at codons 670 and 671 and a Phe for Val substitution at codon 717 (codons numbered according to the APP-770 amino acid isoform); α-sAPP, soluble APP; mAb, monoclonal antibody; PBS, phosphate-buffered saline; FBS, fetal bovine serum; SDS-PAGE, sodium dodecyl sulfate-polyacrylamide gel electrophoresis; DMSO, dimethylsulfoxide.

The terms used herein are intended to have meaning as follows: namely,

"Alkyl" is intended to mean straight, branched-chain or cyclic hydrocarbon chain composed of a number of carbon atoms that is commonly specified according to a formula. Where not specified, alkyl groups in the instant compositions preferably contain about 1 to about 12 carbon atoms ($C_{1-12}$). Representative examples of the subject alkyl groups include methyl, ethyl, propyl, cyclopropyl, isopropyl, n-butyl, t-butyl, sec-butyl, cyclobutyl, pentyl, cyclopentyl, n-hexyl, n-nonyl, n-decyl, cyclohexyl, cyclohexylmethyl, cyclohexylethyl, and the like.

"Alkenyl" is intended to mean a straight, branched-chain or cyclic hydrocarbon chain composed of one or more double-bonded carbon atoms, a number of which carbon atoms is commonly specified according to formula. Where not specified, alkenyl carbon chains in the instant compositions preferably contain about 2 to about 12 carbon atoms ($C_{2-12}$), and preferably about 2 to about 7 carbon atoms ($C_{2-7}$). The subject $C_{2-12}$ alkenyl carbon chains contain about 1 to about 6 double bonds, while $C_{2-7}$ alkenyl carbon chains preferably contain about 1 to about 3 double bonds. Representative alkenyl moieties include 2-methyl-2-propenyl, 2-methyl-1-propenyl, propenyl, 1-butenyl, 2-butenyl, 3-butenyl, 2,2-difluoroethenyl, as well as, those straight and branched chain moieties having up to two double bonds. Cyclic alkenyl carbon moieties preferably contain one or two fused hydrocarbon ring moeities having about 3 to about 16 carbon atoms ($C_{3-16}$), and most preferably having about 4 to about 12 carbon atoms ($C_{4-12}$).

"Alkynyl" is intended to mean a straight, branched-chain or cyclic hydrocarbon chain composed of one or more triple-bonded carbon atoms, a number of which carbon atoms is commonly specified according to formula. Where not specified, alkynyl carbon chains in the instant compositions preferably contain about 2 to about 12 carbon atoms ($C_{2-12}$) with, preferably, about 1 to about 6 triple bonds, and the alkynyl carbon chains of 2 to 6 carbons ($C_{2-6}$), preferably, contain 1 to 3 triple bonds. Representative alkynyl moieties include propynyl. Cyclic carbon alkynyl moieties preferably contain one or two fused hydrocarbon ring moeities having about 3 to about 16 carbon atoms ($C_{3-16}$), and most preferably about 4 to about 12 carbon atoms ($C_{4-12}$). "Lower alkyl", "lower alkenyl" and "lower alkynyl" are intended to mean alkyl, alkenyl and alkynyl hydrocarbon chains, respectively (as defined supra), each of which chains contains fewer than six carbon atoms.

"Cycloalkyl" is intended to mean an unsaturated carbon bond single ring system moiety, or an unsaturated carbon bond multiple cyclic ring system moiety. Preferably, the subject cycloalkyl consists of about 3 to about 10 carbon atoms, and most preferably, the subject cycloalkyl consists of about 3 to about 6 carbon atoms. Representative example of the subject ring system moieties include one, two or more rings that are joined together in a fused, bridged or spiro-connected fashion, each of which moieties may be optionally substituted with one or more alkyl group substituents.

"Cycloalkenyl" is intended to mean a single ring system moiety, or a multiple ring system each of which moieties has at least one carbon-carbon double bond, and each of which moieties preferably contains about 3 to about 10 carbon atoms ($C_{3-10}$), and most preferably, about 4 to about 7 carbon atoms ($C_{4-7}$). Representative example of the subject ring system moieties include one, two or more rings that are joined together in a fused, bridged or spiro-connected fashion, each of which moieties may be optionally substituted with one or more alkyl group substituents.

"Cycloalkynyl" is intended to mean a single ring system moiety, or a multiple ring system each of which moieties has at least one carbon-carbon triple bond, and each of which moieties preferably contains about 3 to about 10 carbon atoms ($C_{3-10}$), and most preferably, about 8 to about 10 carbon atoms ($C_{8-10}$). Representative example of the subject ring system moieties include one, two or more rings that are joined together in a fused, bridged or spiro-connected fashion, each of which moieties may be optionally substituted with one or more alkyl group substituents.

"Heteroatoms" is intended to mean that the subject atoms are not the same. Where not specified, heteroatoms in the instant compositions are commonly non-carbon atoms which are preferably are selected from among Oxygen (O), Nitrogen (N) and Sulfur (S). Substituents containing heteroatoms may be straight chain, branched chain or heterocyclic.

"Aryl" is intended to mean an aromatic hydrocarbon cyclic moiety, specified according to formula. Where not specified, in the instant compositions preferably the aryl moieties contain about 3 to about 14 carbon atoms ($C_{3-14}$) bonded into about 1 to about 2 ring structures. "Lower aryl" is intended to mean that the subject aryl moiety, defined supra, preferably contain about 5 to about 7 carbon atoms in the subject ring structure. "Aralkyl" is intended to mean that the subject aryl moiety, defined supra, is additionally substituted with one or more alkyl groups, as defined supra. Representative examples of aralkyl and aryl moieties include phenyl; benzyl; phenethyl; 1- and 2-naphthylmethyl; 1- and 2-naphthyl; 1- and 2-indenyl; pentalenyl; azulenyl; heptalenyl; acenaphthylenyl; 9-fluorenyl; phenalenyl; phenanthrenyl; anthracenyl; triphenylenyl; pyrenyl, chrysenyl; naphthacenyl; and the like.

"Heterocycle", and "heterocyclic", are intended to mean a cyclic carbon atom ring moiety composed of about 3 to about 14 atoms ($C_{3-14}$), preferably about 3 atoms to about 7 atoms constituting about 1 to about 2 ring moieties; of which atoms, one or more atoms are heteroatoms, as defined supra, and the subject preferred heteroatoms are as set forth above. Representative heterocycles include aliphatic saturated carbon ring moieties bonded with unsaturated heteroaryl ring moieties. Representative examples of heterocycles include pyrrolidinyl, piperidinyl, alkylpiperidinyl, 1,4-dioxanyl, 1,4-dithianyl, 1,4-morpholinyl, 1,4-thiomorpholinyl, 1,2,3-oxadiazolyl, 1,3,5-trithianyl or 1,2,5-triazolyl.

"Heteroaryl" is intended to mean a cyclic carbon atom ring moiety composed of about 3 to about 14 atoms ($C_{3-14}$), preferably about 3 atoms to about 7 atoms constituting about 1 to about 2 ring moieties; of which atoms, one or more atoms is a heteroatom, as defined supra. The subject preferred heteroatoms are as set forth above, and most preferably at least one ring moiety comprises an aromatic ring. Representative examples of heteroaryls include furyl, thienyl, pyridyl, pyrrolyl, N-methylpyrrolyl, pyranyl, indolyl, quinolinyl, isoquinolinyl, cinnolinyl, quinoxalinyl, naphthyridinyl, benzothiazolyl, dibenzothiazolyl, xanthenyl and 1,2,3,4-tetrahydroisoquinolinyl.

"$NR^A R^B$" is intended to mean a chemical moiety in which a nitrogen atom (N) is bonded to both an $R^A$ substituent and an $R^B$ substituent.

In certain alternative embodiments, one or more R group substituents, e.g., $R_3$, $R_5$, and the like, of Formula I, II or III, supra, may be identical with a side chain residue of a "naturally occurring amino acid". "Naturally occurring amino acids", and their constituent "side chain residues" are known in the art. "Natural side chain residues of naturally occurring amino acids", as used herein, is intended to mean natural substituents attached to the α-carbon atom of a naturally occurring amino acid synthesized by a plant or an animal. Representative examples of natural side chain residues include the hydrogen atom attached as a substituent at the α-carbon in glycine, the methyl group attached at the α-carbon in alanine, the isopropyl group attached at the α-carbon in valine, and the like.

"Halogen", "halide" and/or "halo" are used interchangeably to refer substituents selected from among a fluorine atom (F), chlorine atom (Cl), bromine atom (Br), iodine atom (I), as well as pseudohalide atoms. Where not specified, halogen in the instant compositions preferably contain one or more atoms selected from among fluorine, chlorine, bromine and iodine.

"Pseudohalides" is intended to mean atoms, or chemical constituent groups, that have one or more chemical properties and/or chemical reactivities substantially similar to a halogen. The subject constituent groups are distinguished by being interchangeable with halogens in the instant synthetic methods, as disclosed further below. Representative examples of pseudohalides include, but are not limited to, cyanide, cyanate, thiocyanate, selenocyanate, azide and trifluoromethyl.

"Haloalkyl" is intended to mean an alkyl group substituted with one or more halogens.

"Halo-lower alkyl" is intended to mean an alkyl moiety containing six or fewer carbon atoms which is substituted with one or more halogens. Where not explicitly specified otherwise, preferred halo-lower alkyl moieties in the instant compositions are selected from among —$CF_3$, —$CF_2H$, —$CFH_2$, —$CH_2Cl$ and —$CH_2Br$.

"Haloalkoxy" is intended to mean an RO- moiety in which R is a haloalkyl group.

"Aminocarbonyl" is intended to mean an —$C(O)NH_2$ moiety.

"Alkylaminocarbonyl" is intended to mean an —C(O)NHR moiety in which R is hydrogen, alkyl, preferably lower alkyl or aryl, preferably lower aryl.

"Dialkylaminocarbonyl" is intended to mean an —C(O)NR'R moiety in which R' and R are independently alkyl or aryl, preferably lower alkyl or lower aryl;

"Carboxamide" is intended to mean groups of formula —NR'COR.

"Alkoxycarbonyl" is intended to mean an —C(O)OR group in which R is alkyl, preferably lower alkyl or aryl, preferably lower aryl.

"Alkoxy" is intended to mean an RO— group in which R is alkyl, preferably a lower alkyl or aryl, and most preferably a lower aryl.

"Thioalkoxy" is intended to mean and RSO— group in which R is alkyl, preferably a lower alkyl or aryl, and most preferably a lower aryl.

"Alkylene" is intended to mean a straight, branched or cyclic hydrocarbon moiety, preferably a straight or branched moiety composed of about 1 to about 20 carbon atoms ($C_{1-20}$), and most preferably composed of fewer than about 12 carbon atoms ($C_{1-12}$). In presently preferred embodiments, the alkylene moiety is either unsubstituted, or alternatively, is substituted with one or more alkyl groups, as defined supra. In certain alternative embodiments of the invention, the subject hydrocarbon moiety making up an alkylene additionally contains one or more heteroatoms selected from among oxygen and nitrogen. In other embodiments, the latter subject nitrogen heteroatom can constitute an amide nitrogen bonded with an alkyl group. Representative examples of alkylene groups include methylene (—CH$_2$—), ethylene (—CH$_2$CH$_2$—), propylene (—(CH$_2$)$_3$—), cyclohexylene (—C$_6$H$_1$O—), methylenedioxy (—O—CH$_2$—O—) and ethylenedioxy (—O—(CH$_2$)$_2$—O—).

"Lower alkylene" is intended to mean an alkylene moiety composed of fewer than about 6 carbon atoms. In certain preferred embodiments, lower alkylene groups contain about 2 to about 3 carbon atoms.

"Alkenylene" is intended to mean a straight, branched or cyclic hydrocarbon, preferably straight or branched chain composed of about 2 to about 20 carbon atoms (C$_{2-20}$) at least two of which are double bonded one to another. In certain presently preferred embodiments of the invention, the subject alkenylene moiety is preferably composed of about 2 to about 12 carbon atoms (C$_{2-12}$), and in most preferred embodiments the subject moiety preferably consists of a "lower alkenylene" having about 2 to about 6 carbon atoms. In certain alternative embodiments, the subject alkenylene moiety may be composed of a compound substituted at one or more positions in the straight, branched or cyclic hydrocarbon with one or more alkyl groups, as defined supra. In other alternative embodiments, the subject straight, branched or cyclic hydrocarbon may contain one or more heteroatoms, i.e., in place of one or more carbon atoms. In the latter case, the subject heteroatoms are preferably oxygen, sulfur or nitrogen atoms. The latter nitrogen atom may, in other alternative embodiments, constitute an amide nitrogen bonded with an alkyl group. Representative examples of alkenylene groups include —CH=CH—CH=CH—, —CH=CH— and —CH=CH—CH$_2$—.

"Lower alkenylene" is intended to mean an alkenylene having about 2 to about 6 carbon atoms, and preferably about 2 to about 4 carbon atoms.

"Alkynylene" is intended to mean a straight, branched or cyclic hydrocarbon, preferably straight or branched chain composed of about 2 to about 20 carbon atoms (C$_{2-20}$) at least two of which are triple bonded one to another. In certain presently preferred embodiments, the subject alkynylene moiety preferably comprises about 2 to about 12 carbon atoms (C$_{2-12}$), and in most preferred embodiments the subject moiety consists of a "lower alkynylene" having 2 to about 6 carbon atoms. In certain alternative embodiments, the subject alkynylene moiety may be composed of a compound substituted at one or more positions in the straight, branched or cyclic hydrocarbon with one or more alkyl groups. In other alternative embodiments, the subject straight, branched or cyclic hydrocarbon may contain one or more heteroatoms, i.e., in place of one or more carbon atoms. The latter heteroatoms are preferably oxygen, sulfur or nitrogen atoms. The latter nitrogen may, in other alternative embodiments, constitute an amide nitrogen bonded with an "alkyl group substituent", as defined below. Representative examples of alkynylene groups include —C≡C—C≡C—, —C≡C— and —C≡C—CH$_2$—.

"Lower alkynylene" is intended to mean an alkynylene composed of about 2 to about 6 carbons. In presently preferably embodiments of the invention, lower alkynylene moieties are composed of about 2 to about 4 carbon atoms.

"Arylene" is intended to mean a monocyclic or polycyclic hydrocarbon ring moiety having one or more aromatic/aryl groups as constituents in the subject ring moiety, and additionally, having one or more carbon-carbon double bonds. The arylene moiety is preferably composed of 3 to about 20 carbon atoms (C$_{3-20}$). In presently most preferred embodiments, the subject arylene groups are composed of about 3 to about 12 carbon atoms (C$_{3-12}$), and most preferably, the arylene group is a "lower arylene" (C$_{5-6}$). In alternative embodiments, the subject arylene moiety may, in turn, be substituted with one or more aryl groups, and the arylene cyclic ring form may also, optionally, contain one or more heteroatoms. The latter heteroatoms constituting the arylene cyclic ring are preferably oxygen, sulfur or nitrogen, and the subject nitrogen atom may, in other embodiments, constitute an amide nitrogen bonded to an "alkyl group substituent". Representative examples of arylene groups include 1,2-, 1,3- and 1,4-phenylenediamine.

"Lower arylene" is intended to mean an arylene group having about 8 to about 10 carbon atoms (C$_{8-10}$).

"Alkylidene" is intended to mean a =CR'R" substituent group, in this case, attached to a basal hydrocarbon core structure such as a =CR'R" group substituent of an alkylene or a heterocycleene. In the latter case, the =CR'R" substituent group is attached to the core structure through the group's carbon-carbon double bond (=C—). Representative examples of alkylidene groups include methylidene (=CH$_2$) and ethylidene (=CHCH$_3$).

"Arylalkylidene" is intended to mean an alkylidene group, i.e., =CR'R", in which either the R' or the R" substituent constitutes an aryl group.

"Carbonyl" is intended to mean a bivalent carbonyl group of the general formula (—(C=O)—).

"Alkyl group substituent" is intended to mean a hydrocarbon, a halo-hydrocarbon or a halogen-containing substituent to a core structure as follows: namely, in presently preferred embodiments, the subject "alkyl group substituent" is halo-lower-alkyl, aryl, hydroxy, alkoxy, aryloxy, alkylthio, arylthio, aralkyloxy, aralkylthio, carboxy, alkoxycarbonyl, an oxygen atom or a cycloalkyl group.

"Aryl group substituent", when used in regard to a core structure that is alkyl, cycloalkyl, cycloalkylalkyl, aryl, or a heteroaryl moiety, is intended to mean that the subject core structure is substituted with 1 or more, and preferably 1 to about 3, "aryl group substituents" selected from the following: namely, halogen atoms, alkyls, halo-alkyls, arylalkyl, heteroarylalkyl, alkenylene, alkynylene and hydroxyl. In presently preferred embodiments of the invention wherein the core structure is a halo-lower-alkyl, the preferred "aryl group substituents" are trifluoromethyl, formyl, alkylcarbonyl or substituted ore unsubstituted arylcarbonyl. In the latter case the substituents comprise 1 or more, and preferably 1 to about 3 groups selected from among the following: namely, halogen atoms, halo-alkyls, alkyls, heteroarylcarbonyls, carboxyls; alkoxycarbonyls, aryloxycarbonyls, aminocarbonyls, alkylaminocarbonyls, dialkylaminocarbonyls, arylamino-carbonyls, diarylaminocarbonyls, arylalkylaminocarbonyls, alkoxys, aryloxys, perfluoroalkoxys, alkenyloxys, alkynyloxys, arylalkoxys, aminoalkyls, alkylaminoalkyls, dialkylaminoalkyls, arylaminoalkyls, amino groups, alkylamino groups, dialkylamino groups, arylaminos, alkylarylaminos, alkylcarbonylaminos, arylcarbonyls-, amines, azidos, nitrogen atoms, thiol groups, alkylthiol groups, arylthiols, perfluoroalkylthiols, thiocyano groups, isothiocyano groups, alkylsulfinyl groups, alkylsulfonyls, arylsulfinyls, arylsulfonyls, aminosulfonyls, alkylaminosulfonyls, dialkylaminosulfonyls and arylaminosulfonyl groups.

"Aminosulfonyl" is intended to mean either an —NHSO$_2$— substituent or an —SO$_2$NH— bivalent group.

"Amido" is intended to mean either a —C(O)NH— or an —HNC(O)— bivalent group.

"Thioamido" is intended to mean either a —C(S)NH— or an —HNC(S)— bivalent group.

"Oxyamido" is intended to mean a —OC(O)NH— or an —HNC(O)O— bivalent group.

"Thiaamido" is intended to mean a —SC(O)NH— or an —HNC(O)S— bivalent group.

"Dithiaamido" is intended to mean a —SC(S)NH— or an —HNC(S)S— bivalent group.

"Ureido" is intended to mean an —HNCONH— bivalent group.

"Thioureido" is intended to mean an —HNCSNH— bivalent group.

"Alzheimer's disease" is the most common form of dementia affecting nearly 25% of the elderly population over the age of 85 years. Alzheimer's disease (AD) can now be diagnosed with a considerable degree of accuracy with 90% correspondence between clinical diagnosis and autopsy confirmation at certain centers. The characteristic histopathologic changes at autopsy include neurofibrillary tangles, neuritic "senile" plaques, neuronal loss and amyloid angiopathy (1). The major constituent of plaques (plaques) is a 4.2 kDa fibrillogenic polypeptide of 42–43 amino acids in length and referred to as amyloid beta-protein (abbreviated A$\beta$). A$\beta$ is derived by proteolytic cleavage from amyloid precursor protein (APP; 2–5) and accumulates in the cerebral extracellular perivascular matix in patients with AD, where its observance is considered to be a pathological landmark of the disease. When aggregated in fibrillar beta-pleated sheet configurations, A$\beta$ is thought to form a nidus for binding of other proteins that may contribute to pathology. Binding of A$\beta$ to neurons can result in increased vulnerability to excitotoxicity, generation of oxygen free radicals, impaired membrane transport systems, inhibition of glutamate receptors and induction of apoptosis (6). Neuronal loss can lead to disruption and defects in neurotransmission, cell-cell communications and abnormal production of extracellular matrix proteins. In addition, deposition of A$\beta$ in and around cerebral blood vessels, i.e., cerebral amyloid angiopathy, has been associated with hemorrhagic stroke in the elderly and patients with AD.

"Amyloid precursor protein". Abbreviated APP, is intended to mean an amino acid sequence of National Library of Medicine Accession No. 1070623, having 695 or 770 amino acids, and sequences related thereto e.g. by conservative amino acid substitution and the like Representative proteins have one or more of the following attributes: namely, a calculated theoretical molecular weight about 86,943 encoded by a gene mapping to 21q21.2 and 2-21q21.2, alternatively spliced to encode either a protein of 695aa or 770aa as a C-terminal extended polypeptide with a Kunitz-type serine protease inhibitor doimain, Gly700-Leu$_{723}$ being the transmembrane domain, and Lys$_{723}$-Phe$_{695}$ or Lys$_{723}$-Asn$_{770}$ being the cytoplasmic domain.

"A$\beta$ domain", also referred to as A$\beta$-peptide", and abbreviated "A$\beta$", is intended to mean a cleavage product of APP, supra, as mediated by one or more proteases at an APP NH$_2$-terminal Lys$_{670}$-Met$_{671}$ or Met$_{671}$-Asp$_{672}$ residue and a COOH-terminal Val$_{710}$-Va$_{711}$ or at a COOH-terminal Ala$_{713}$-Thr$_{714}$. "A$\beta_{1-40}$" being Asp$_{672}$-Ile$_{712}$; "A$\beta_{1-39}$" being Asp$_{672}$-Val$_{711}$; A$\beta_{1-42}$ being Asp$_{672}$-Thr$_{714}$; and "A$\beta_{1-43}$" being Asp$_{672}$-Val$_{715}$.

A "Carboxy terminal fragment", abbreviated interchangeably CTF and i$\beta$-CTF, is intended to mean the portion of APP (Accession No. 1070623) corresponding to an APP fragment having a molecular size on SDS-PAGE of about 9 kDa to about 12 kDa and/or a sequence from about Asp$_{672}$ to about Asn$_{770}$.

"CTF 100", meaning carboxy terminal fragment of 100 amino acids in length, is intended to mean an APP fragment having an apparent molecular size on SDS-PAGE of about 9 kDa to about 12 kDa and a sequence from about Asp$_{672}$ to about Asn$_{770}$.

"Soluble APP", abbreviated sAPP, is intended to mean the portion of APP (Accession No. 1070623) corresponding to an N-terminal fragment produced by $\alpha$-secretase having a molecular size on SDS-PAGE of about 100 kDa to about 115 kDa and lacking the transmembrane (supra) and cytoplasmic (supra) domains of APP.

"Treatment" is intended to mean a method of delivering to a subject in need thereof a pharmaceutical preparation according to the compounds of the invention with the aim of effecting a change in APP:A$\beta$ processing in the subject in need thereof. The instant methods include delivering the preparation to a patient i) before the dysfunction has been diagnosed, e.g., prophylactic protocols delivered with the aim of preventing development of the dysfunction, as well as, ii) after the dysfunction has been diagnosed, e.g., therapeutic protocols. That the subject treatments have fulfilled the intended aim of effecting a change in APP processing to A$\beta$ in the subject will be evident by one or more of the following: namely, (i) a change in the amount of A$\beta$ or sAPP in a sample of a biological tissue or biological fluid collected from a treated patient; (ii) a change in the amount of one or more APP:A$\beta$ processing proteins in a biological tissue or biological fluid collected from a treated patient; or, (iii) a change (increase or decrease) or complete elimination of one or more clinical indicia of disease, e.g., diagnostic symptoms, in a treated patient.

"Dysfunction" is intended to mean a pathologic condition of APP processing to A$\beta$ in a tissue, i.e., one or more changes in APP processing and/or production of A$\beta$ as compared with the processing of APP occurring in a normal healthy control cohort. For example the subject pathological conditions include, but are not limited to, i) toxic amyloid dystrophy, (e.g., chemical or drug-induced secondary amyloid dystrophy), ii) vascular impairment with amyloid deposition, iii) degeneration and peripheral degeneration of vascular and/or neural tissue associated with amyloid deposition, iv) cellular detachment from basement membrane and defects in tissue organization visible microscopically in histology sections, e.g., in the endothelium of vessels; v) amyloid containing lesions resulting following physical trauma; and v) hereditary amyloid deposition in tissues, e.g., systemic amyloidosis and familial Alzheimer's diseases.

"Subject in need thereof" is intended to mean a mammal, e.g., humans, domestic animals and livestock, having one or more dysfunctions of APP processing, as defined above.

"Biological fluid" as used herein is intended to mean a tissue fluid, such as cerebrospinal fluid (CSF); blood, plasma and serum; fluid collected from a body cavity (i.e., peritoneal fluid, lung lavage fluid, urogenital mucus secretions, and the like); urine, feces, sputum, sweat; and the like.

"Processing of APP to A$\beta$", abbreviated APP:A$\beta$ processing, is intended to mean intracellular pathways by which proteases act upon APP to catalyze hydrolysis of peptide bonds thereby liberating the A$\beta$ fragment (as defined supra) of APP; in this case, including processes active in the following intracellular compartments: namely, in the endoplasmic reticulum; in the cytoplasm associated with ribosomes; in cytoplasmic vesicles (e.g., Golgi secretory vesicles); and, in lysosomal vesicles and the like.

"Substantially pure" is intended to mean that the subject preparation is sufficiently homogeneous to appear free of detectable impurities as determined by standard methods of physicochemical analysis, e.g. IR, NMR, spectral methods for determining chirality and the like, or by separation methods, e.g., thin layer chromatography (TLC), high performance liquid chromatography (HPLC), gas liquid chromatography (GLC) such as subject to analysis by mass spectrometry (GCMS), or by another method employed to assess chemical purity. A substantially chemically pure compound may, however, be a mixture of stereoisomers. In such instances, further purification may increase the specific activity of the compound e.g. by isolating a single isostere.

"Prodrug" is intended to mean one or more of the instant compounds in a form that, upon in vivo administration, is metabolized and/or otherwise converted from a form lacking in a biological or pharmaceutical activity, into a form having the subject activity. Representative examples of forms of prodrugs are disclosed e.g. in Nogrady (1985) *Medicinal Chemistry A Biochemical Approach*, Oxford University Press, New York, at pages 388–392.

"Isostereoisomer", abbreviated isostere, is intended to mean of a compound possessing of one of two or more stereochemical attributes expressed by one of the instant compounds, e.g. one spectral property. An isostere compound may exhibit a biologic and/or a pharmacologic activity that is greater than, or less than that of a racemic mixture of one of the instant compounds.

"Alter APP processing to Aβ", is intended to mean altering the processing of APP. Two alternative processing pathways for APP may be represented as follows (the arrows represent cleavage sites):

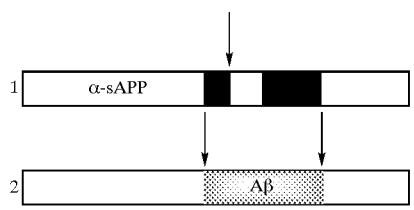

"Altering processing of APP to Aβ", abbreviated altering APP:Aβ processing, when used in regard to a composition containing one or more of the instant compounds is intended to mean that the subject composition is effective when administered to a cell, e.g., in tissue culture, to inhibit the production of carboxy terminal fragments of APP including iβ-CTF and/or Aβ. While not wishing to be tied to any particular mechanism of action, representative examples of mechanisms by which the latter inhibitory effect on Aβ production may be exerted by the instant compounds include inhibiting: (a) an enzyme activity in a cell, e.g., an enzyme exhibiting a γ-secretase activity; (b) a co-factor binding to, and exerting an effect on, the subject enzyme activity in the cell, e.g., a co-factor increasing the catalytic efficiency or turnover rate of an enzyme with, a γ-secretase activity in a cell; (c) a transcription regulator, e.g., altering the level of expression of mRNA encoding the subject enzyme or cofactor protein in a cell; (d) a protein kinase, e.g., altering either the level of expression of, or the activity of, the subject enzyme in a cell; and (e) a phosphorylase, e.g., altering the activity of the subject enzyme in the cell. The subject compositions may act directly on enzyme:cofactor:APP substrate complexes, or they may act indirectly, i.e., to change transcription or translation of enzyme proteins or cofactors.

"Altering apoptosis" is intended to mean that the subject compound is effective to inhibit a cysteinyl protease activated in a cell which has been treated to induce programmed cell death. Representative proteases so activated include calpains, caspases (e.g., caspases 3, 8 and 9), cathepsins and the like. Representative apoptosis inducer agents so able to induce apoptosis include Fas antibody, staurosporine, interleukins IL-1 and TNF, glucose and oxygen deprivation during ischemic tissue injury and the like. Apoptosis may be induced in the cells of tissues subject to traumatic injury, restricted blood flow (e.g., during peripheral microvascular clotting and stroke) and the like.

"Apoptosis" is intended to mean the cascade of energy (ATP) dependent events triggered by an apoptosis inducer agent and leading to programmed cell death through mechanisms commonly involving intracellular caspase enzymes, and commonly requiring about 12 to about 24 hours to accomplish the subject cell death. Apoptosis does not involve rapid, non-energy dependent lysis of cells, such as occurs during necrosis with release of cellular constituents (e.g., LDH) into the extracellular space. However, during apoptosis cells fragment their DNA and package it into membrane vesicles.

Embodiments of the invention provide presently preferred compounds of FORMULA I, II and III as set forth according to FORMULAS IV, V and VI: as follows, namely,

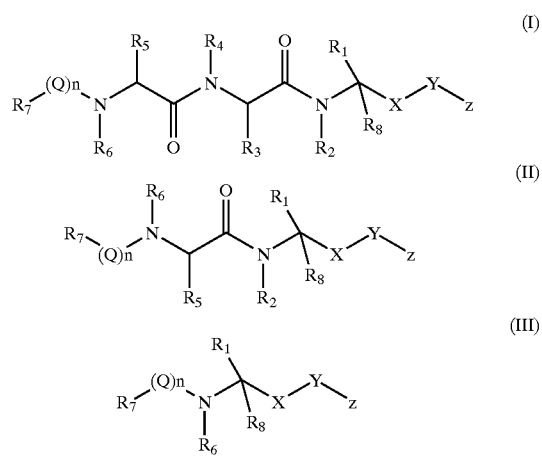

wherein, all of the groups and substituents thereof, e.g. $R_1$–$R_8$, Q, Y and Z are identical with those set forth in regard to FORMULA I, II and III, above. In certain alternative preferred embodiments of compounds according to FORMULA IV, V or VI, when (Q)n is a carbonyl group and $R_1$ and $R_7$ and the atoms to which they are attached form a heterocyclic ring moiety, the presently preferred ring moieties are succinimide, phthalimide or maleimide, and the most preferred is phthalimide. Similarly, when n is zero and $R_1$, $R_7$ and the atoms to which they are attached form a heterocyclic ring moiety, the preferred heterocyclic ring moieties are morpholino, thiomorpholino, pyrrolidinyl and V-substituted pyrrolidinyl, and most preferably 4-hydroxypyrrolidinyl and 1,2,3,4-tetrahydroisoquinolinyl. When n is zero and $R_3$, $R_1$ or $R_2$, and $R_7$ taken together with the atoms to which they are attached form heterocyclic moieties, then the preferred ring moieties are morpholino, thiomorpholino, pyrrolidinyl, and V-substituted pyrrolidinyl, and most preferred is 4-hydroxypyrrolidinyl. Representative examples of the presently preferred compounds include: e.g., N-Cbz-L-Leu-L-Leu-L-Leuene-phenyl vinyl sulfone; N-Cbz-L-Leu-L-Leu-D-Leuene-phenyl vinyl sulfone; N-(THIQ-carbonyl)-L-Leu-L-Leu-D-Leuene phenyl vinyl sulfone; N-(THIQ-carbonyl)-L-Leu-L-Leu-L-Leuene phenyl vinyl sulfone, N-(THIQ-carbonyl)-L-Val-L-Met-L-Leuene phenyl vinyl sulfone; N-(THIQ-carbonyl)-L-Val-L-Met-D-Leuene phenyl vinyl sulfone; N-(THIQ-carbonyl)-L-Val-L-Leu-L-Leuene phenyl vinyl sulfone; N-(THIQ-carbonyl)-L-Val-L-Leu-D-Leuene phenyl vinyl sulfone; N-(4-benzylpiperidinyl-carbonyl)-L-Leu-L-Leu-L-Leuene phenyl vinyl sulfone; N-(4-benzylpiperidinyl-carbonyl)-L-Leu-L-Leu-D-Leuene phenyl vinyl sulfone; N-(4-benzylpiperazinyl-carbonyl)-L-Leu-L-Leu-L-Leuene phenyl vinyl sulfone; and, N-(4-benzylpiperazinyl-carbonyl)-L-Leu-L-Leu-D-Leuene phenyl vinyl sulfone.

Embodiments of the invention provide pharmaceutical compositions in which the instant compounds are present as the salts of organic acids and bases (such as acetates, lactates, tartrates, citrates, ascorbates, succinates, butyrates, valerates, fumarates and the like); salts of inorganic acids and bases, e.g., alkali metal salts of lithium, potassium, sodium, alkaline earth metals, such as barium, calcium and magnesium and the like, salts of transition metals such as Zinc, salts of mineral acids such as hydrochlorides and sulfates; esters; acids; bases; solvates; hydrates; amine salts; phosphonates such as sodium hydrogen phosphate and disodium phosphate, and the like; including hydrolyzable prodrugs cleavable and activated in vivo to drugs, e.g., derivatives of N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methylbenzimidazole, diethyl amine and other alkylamines, piperazine and tris(hydroxymethyl) aminomethane and the like.

In other embodiments the invention provides a pharmaceutical preparation consisting of one or more isolated and substantially pure diastereoisomers or chiral forms of a pharmaceutical preparations according to FORMULA (I), (II) and/or (III).

Embodiments of the invention provide compounds according to FORMULA I, II or III that are effective to modulate the activity of cysteinyl proteases including extracellular (secreted) proteases and intracellular protease involved in protein processing. The instant protease inhibitors include inhibitors acting, e.g., by processes including both competitive and non-competitive inhibition.

In yet other embodiments, the invention provides methods for administering to a subject in need thereof a concentration of one or more pharmaceutical preparations consisting of one or more compound according to FORMULA I, II and/or III that is effective to ameliorate one or more symptoms of disease. Examples of subjects so-in-need include e.g. patients with systemic amyloidosis, Alzheimer's disease, atherosclerosis, restenosis following angioplasty, rheumatoid arthritis and connective tissue diseases, dermatologic diseases such as Epidermolysis bullosis, Systemic lupus erythematosus, Sjogren's syndrome, Insulin-dependent diabetes types I and II, atherosclerosis, stroke, traumatic neural degeneration, chronic vascular and respiratory disorders, necrotic and apoptotic tissue damage resulting from bacterial, fungal and viral infection, (e.g., AIDS dementia, adenovirus, HSV, HPV, *influenza* and the like), inflammatory bowel disease, irritable bowel syndrome, diarrhea, constipation, gastric acid secretion and ulcers, complications resulting from co-medication or surgical procedures; or heart insufficiency, hyperprolactinemia, asthma and arthritis.

Embodiments also provide compounds according to FORMULA I, II or III, that are capable of inhibiting the activity of a cysteinyl protease, e.g., an intracellular secretase such as β-secretase involved in processing of APP and production of Aβ, an intracellular apopain/caspase protease involved in programmed cell death (apoptosis), an intracellular protease involved in antigen processing, e.g. a cathepsin, or an extracellular protease involved in tissue destructive processes, e.g., in trauma or arthritis. That a compound is so active may be determined by conducting e.g. either an in vitro or an in vivo assay. For example, in an in vitro assay the instant compounds decrease in the activity of a cellular cysteinyl protease enzyme activity, or a secreted extracellular cysteinyl protease. Assays for cysteinyl proteases, as with assays for other proteases, are within the ordinary skill in the art. In one representative example, the subject cysteinyl protease is an intracellular β-secretase enzyme involved in processing of APP and production of Aβ amyloidogenic polypeptides. In the latter case a positive assay is recorded when one or more of the following are observed: namely, (1) a decrease is observed in the 4-kDa amyloid Aβ in the medium relative to control cultures; and/or (2) the relative amount of sAPP, in the medium is observed to increase; (3) a decrease is observed in the amount of C-terminal APP fragments >9 kDa in cell lysates, i.e., resulting from differential processing; and/or (4) there is an observed increase in the amount of α-sAPP in the medium relative to control cultures. In vivo, the instant compounds are preferably effective when administered to an experimental animal of Aβ or systemic amyloidosis to either: (1) increase the levels of sAPP (e.g., in brain, plasma or CSF), and/or (2) decrease the level Aβ in a biological fluid or tissue extract. In one representative example, a positive assay result may be indicated as an increase in the ratio of α-sAPP to sAPP in a tissue sample from a pre-treatment to a post-treatment interval.

Representative methods for preparing the instant vinyl sulfones are depicted in the EXAMPLES, section below, and in particular in Reaction Schemes A–F of EXAMPLES 1–14. In Scheme A, preparation of amino ester hydrochlorides is depicted; Scheme B illustrates preparation of vinyl sulfones from the amino ester hydrochlorides; in Scheme C, formation of di- and tri-peptide vinyl sulfone analogs is depicted; Scheme D illustrates the preparation of an illustrative isomer of an amino vinyl sulfone; and, synthesis of illustrative N-protected tripeptide vinyl sulfone analogs as 1,2,3,4-tetrahydro-isoquinolinyl ureas is shown in Scheme E. An alternative to the synthesis of Scheme E is presented in Scheme F, i.e., 4-benzylpiperidine or 1-benzylpiperazine are substituted for 1,2,3,4,5-tetra-hydroisoquinoline. As an alternative, an automated peptide synthesizer and solid phase sequential coupling procedures may be used to produce intermediates useful in final synthesis of the instant di- and tri-peptide inhibitors. For example, the instant compounds may be synthesized from their carboxyl terminal end toward their amino terminal end using sequentially protected amino acids, amino acid derivatives and/or isomers, or spacer groups, according to the structure set forth in FORMULAS I, II and/or III. A variety of solid phase resin supports are useful in this method including certain of those useful in the art for solid phase synthesis of peptides. One presently preferred resin comprises polystyrene cross-linked with from about 0.5% to about 3% modified divinyl benzene, wherein the modification involves benzhydrylamidation, chloromethylation or hydroxymethylation. Modification is effective to produce sites that are useful for linking the instant di- and tri-peptide intermediates, e.g., through amide or ester bonds. One representative example of a hydroxymethyl resin is disclosed by Bodansky et al. W 966) *Chem. Ind.* (London) 38:1597–98). Preparation of illustrative chloromethyl- and benzhydrylamine-resins is disclosed in Stewart et al. ("*Solid Phase Peptide Synthesis*" 2nd Edition, Pierce Chemical Co., Rockford, Ill. (1984), Chapter 2, pp. 54–55). Illustrative methods for coupling protected amino acids to a resin are disclosed by Gisin ((1973) *Helv. Chem. Acta* 56:1476).

A variety of α-amino protecting groups may be useful in synthesis of the instant compounds and their intermediates. Representative examples of such protecting groups as presently contemplated include: (i) acyl protecting groups such as formyl, trifluoroacetyl, benzoyl, phthalyl, p-toluenesulfonyl (tosyl), benzenesulfonyl, nitrophenylsulfonyl, tritylsulfonyl, o-nitrophenoxyacetyl, α-chlorobutyrl, 4-((4-chloro-phenyl) sulfonylaminocarbonyl)phenylcarbonyl, and 4-((4-bromophenyl)sulfonylaminocarbonyl)phenylcarbonyl; (ii) aromatic urethane protecting groups such as phenyloxycarbonyl, benzyloxycarbonyl and substituted benzyloxycarbonyls such as p-chlorobenzy[oxycarbonyl, p-methoxybenzy-[oxycarbonyl, p-nitrobenzyloxycarbonyl, p-bromobenzyloxycarbonyl, 1-(p-biphenyl)-1-methylethoxycarbonyl, α,α-dimethyl-3,5-dimethoxybenzyloxycarbonyl, and benzhydryloxycarbonyl; (iii) aliphatic urethane protecting groups such as t-butyloxycarbonyl (Boc), diisopropylmethoxycarbonyl, isopropyloxy-carbonyl, methoxycarbonyl, ethoxycarbonyl, isobutyloxycarbonyl and allyloxycarbonyl; (iv) cycloalkyl urethane protecting groups such as cyclopentyloxycarbonyl, adamantyloxycarbonyl, and cyclohexyloxycarbonyl; (v) thiourethane protecting groups such as phenylthiocarbonyl; (vi) alkyl type protecting groups such as triphenylmethyl (trityl) and benzyl (Bn); and (vii) alkyl and aryl silyl protecting groups such as trimethylsilyl, tert-butyidimethylsilyl, tert-butyl-diphenylsilyl and triisopropylsilyl. t-butyloxycarbonyl (Boc) is one presently preferred α-amino protecting group. Representative methods using Boc for protecting are disclosed by Bodansky et al. in "The Practice of Peptide Synthesis," Springer-Verlag, Berlin (1984), p. 20). The selection and use of an appropriate coupling reagent is within the skill in the art. Particularly suitable coupling reagents where the amino acid to be added is Gln, Asn, or Arg include N,N-dicyclohexyl-carbodiimide and 1-hydroxybenzotriazole. The use of the latter reagents during synthesis of the instant compounds of FORMULA I, II and/or III prevents nitrile and lactam formation. Other suitable coupling agents include e.g., (i) carbodiimides such as 1-(3-dimethylamino-propyl)-3-tehyl-carbodiimide hydrochloride); (ii) ketenimines; (iii) isoxazolium salts such as N-ethyl-5-phenyl-isoxazolium-3-sulfonate; (iv) monocyclic nitrogen-containing heterocyclic amides of aromatic character containing 1–4 ring nitrogen atoms, e.g., imidazolides, pyrazolides and 1,2,4-triazolides, and particularly N,N-carbonyldiimidazole and N,N-carbonyl-di-1,2,4-triazole; (v) alkoxylated acetylene e.g., ethoxyacetylene; (vi) reagents which form a mixed anhydride with the carboxyl moiety of the amino acid, e.g., ethyl chloroformate and isobutyl chloroformate, or alternatively, the symmetrical anhydride of an amino acid to be coupled e.g., Boc-Ala-O-Ala-Boc; and (vii) nitrogen-containing heterocyclic compounds having a hydroxyl group on one ring nitrogen, e.g., N-hydroxyphthalimide, N-hydroxysuccinimide and 1-hydroxybenzotriazole. Activating reagents, and methods of their use in peptide coupling, are known in the art, e.g. as disclosed in Kapoor ((1970) *J. Pharm. Sci.* 59:1–27). For synthesis of the instant compounds according to FORMULAS I, II and/or III, presently preferred coupling agents are symmetrical anhydrides. For removal of a compound from a preferred benzhydrylamine resin, treatment with a solution of dimethyl sulfide, p-cresol, thiocresol, or anisole in anhydrous hydrogen fluoride is presently preferred. The cleavage reaction is also preferably carried out at a temperature between about 0° C. and about room temperature, over a period of about 5 minutes to about 5 hours.

Embodiments of the invention provide pharmaceutical compositions comprising one or more compounds according to FORMULA I, II and/or III, above. Preferably, each of the instant compounds present in the pharmaceutical composition is present in a therapeutically effective amount. The instant pharmaceutical compositions find a variety of uses in treatments for neurological disorders, e.g., schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy; as well as in treatments of other diseases, e.g., cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers. The instant pharmaceutical compositions may also be useful as co-medication in surgical procedures and pheochromocytoma; or in co-treatments of heart insufficiency, hyperprolactinernia, bacterial infections, asthma or arthritis.

The instant pharmaceutical compositions are preferably formulated as solutions, suspensions, tablets, dispersible tablets, pills, capsules, powders, sustained release formulations or elixirs. As such the compositions are useful for oral administration, or in sterile solutions or suspensions, for parenteral administration. Transdermal delivery, e.g., patch preparations, and dry powder inhalers are also contemplated. Examples of methods that may be useful for formulating the instant pharmaceutical compositions are disclosed e.g., by Ansel, *Introduction to Pharmaceutical Dosage Forms, Fourth Edition* 1985, p. 126. The instant pharmaceutical compositions may be formulated as the sole pharmaceutically active ingredient in the composition or may be combined with other active ingredients. Liposome delivery systems are also contemplated, e.g., as disclosed in U.S. Pat. No. 4,522,811.

The concentration of active compound(s) in the instant pharmaceutical composition will depend on absorption, inactivation and excretion rates of the active compound(s) (i.e., the selected compounds of FORMULA I, II and/or III, above), the physicochemical characteristics of the compound(s), the dosage schedule, and amount administered as well as other factors known to skilled artisans. Typically a therapeutically effective dosage will produce a serum concentration of one or more of the instant compounds ranging from about 0.1 ng/ml to about 50–100 $\mu$g/ml serum or plasma. The pharmaceutical compositions typically should provide a dosage of from about 0.001 mg to about 2000 mg of compound per kilogram (kg) of body weight per day. Pharmaceutical dosage unit forms may be prepared to provide about 1 mg to about 1000 mg, preferably about 10 mg to about 500 mg of the instant compound. The dosage and method of treatment will be determined by the physician after consideration of the general health, size and condition of a patient.

Effective concentrations (or amounts) of one or more of the compounds described herein or pharmaceutically acceptable derivatives thereof may be mixed with one or more suitable pharmaceutical carriers or vehicles. Solutions or suspensions useful for parenteral, intradermal, subcutaneous, or topical administration may include a sterile diluent such as water for injection, saline solution; a fixed oil; a polyethylene glycol; a glycerin; a propylene glycol or other synthetic solvent; one or more antimicrobial agents, e.g. benzyl alcohol and methyl parabens; an antioxidant, e.g. ascorbic acid or sodium bisulfite; a chelating agent, e.g. ethylenediaminetetraacetic acid (EDTA); a buffer, e.g. an acetate, citrate or phosphate buffer; or, an isotonic agent e.g., sodium chloride or dextrose. Parenteral preparations may be enclosed in ampules, disposable syringes or single or multiple dose vials made of glass, plastic or other suitable materials.

Methods for improving the solubility of the instant compounds, e.g., during administration and delivery from within the instant pharmaceutical compositions, include but are not limited to, uses of co-solvents, e.g., dimethylsulfoxide (DMSO), surfactants, e.g., TWEEN, dissolution in aqueous sodium bicarbonate, and preparation of soluble derivatives or prodrugs of the instant compounds prior to formulation.

Unit dosage forms suitable for administration to subjects in need thereof, e.g., as packaged individually, are known in the art. Each unit-dose commonly contains a predetermined quantity of the therapeutically active compound sufficient to produce a desired therapeutic effect; in association with the required pharmaceutical carrier, vehicle or diluent. Examples of unit-dose forms include ampoules and syringes and individually packaged tablets or capsules. Unit-dose forms may be administered in fractions or multiples thereof. Representative methods for preparing dosage forms are known in the art, e.g., see *Remington's Pharmaceutical Sciences*, Mack Publishing Company, Easton, Pa., 15th Edition, 1975.

Oral pharmaceutical dosage forms including solid, gel and liquid are contemplated formed as tablets, capsules, granules, bulk powders, chewable lozenges enteric-coated capsules, sugar-coated or film-coated capsules, hard or soft gelatin capsules, granules e.g., as non-effervescent or effervescent forms, pills, troches and the like. Liquid oral dosage forms include aqueous solutions, emulsions, suspensions, solutions and/or suspensions reconstituted from non-effervescent granules and effervescent preparations reconstituted from effervescent granules.

Parenteral injectables can be prepared in conventional forms, either as liquid solutions or suspensions, solid forms suitable for solution or suspension in liquid prior to injection, or as emulsions. Typically a therapeutically effective dosage is formulated to contain a concentration of at least about 0.1% w/w up to about 90% w/w or more, preferably more than 1% w/w of the active compound to the treated tissue(s).

Topical solutions, suspension, emulsions and the like may be formulated as creams, gels, ointments, emulsions, solutions, elixirs, lotions, suspensions, tinctures, pastes, foams, irrigations, sprays, nasal sprays, suppositories, bandages, dermal patches, transdermal delivery systems and the like. Contemplated formulations include inhalent aerosols in the form of an aerosol or nebulizer solutions, inhalent therapy solutions, microfine powders for insufflation, and the like. Also contemplated are formulations for skin and mucous membranes, ophthalmic uses (e.g., eyes), intracisternal and intra-spinal application.

The pharmaceutical compositions containing compounds or pharmaceutically acceptable derivatives may be packaged as articles of manufacture containing e.g., a packaging material; the instant pharmaceutical composition; a product insert describing that the composition is effective in ameliorating one or more symptoms of disease, i.e., as set forth above; and, a label indicating that the composition containing the compound or derivative thereof is useful in the treatment or prevention of the disease, i.e., as set forth above.

Embodiments of the invention provide compounds according to FORMULA I, II and/or III that find uses in pharmaceutical compositions manufactured for the purpose of administering a treatment effective in altering apoptosis and altering processing of APP to A$\beta$, e.g., altering deposition of amyloid. The dose ranges, which can be established empirically, for use in the treatment of disease states will depend upon the etiology, nature, and severity of the disease state as well as such other factors as determined by the attending physician. The broad range for effective treatment is about 0.01 to 10 mg per kilogram (kg) of body weight per day. The preferred range is about 0.1 to 10 mg/kg of body weight per day. Preferred modes of administration include oral and parenteral modes of administration. It is believed that the instant treatments for patients with such amyloid disorders will effect beneficial changes in the disease process resulting in a stabilization of disease activity, slowed progression of disease, and/or an enhanced lifestyle with increased cognitive ability and decreased anxiety, as well as a possible delay (or obviation) of the need to institutionalize certain patients.

In other embodiments, pharmaceutical compositions are provided comprising the instant compounds of FORMULA I, II and/or III as formulated for use to alter apoptosis, e.g., by inhibiting the action of cysteinyl caspase proteases and/or cathepsin proteases. $Ca^{2+}$ dependent proteases are presently thought to play significant roles in the pathology of a variety of disorders, including cerebral ischaemia, cataract, myocardial ischaernia, muscular dystrophy and platelet aggregation.

The following examples are included for illustrative purposes only and are not intended to limit the scope of the invention.

EXAMPLE 1

Solution Phase Synthesis
(2RS)-2-tert-Butoxycarbonylaniino-4-methyl-4-pentenoic Acid A. Ethyl (2RS)-2-Diphenylmethylenamino-4-methyl-4-pentenoate

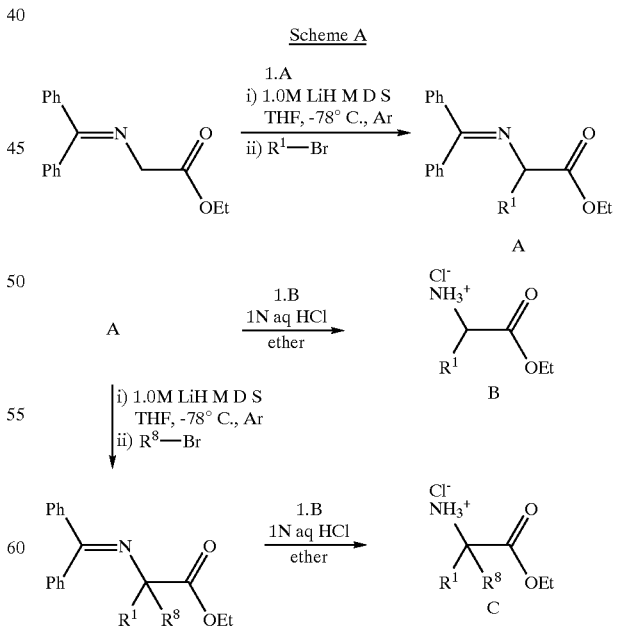

To a stirred solution of N-(diphenylmethylene)glycine ethyl ester (available from Aldrich Chemical Co., Milwaukee, Wis.) (50.0 g, 187 mmol) in dry THF (200 mL)

at −78° C. under argon was added a 1.0 M solution of lithium bis(trimethylsilyl)amide (Li HMDS; 210 mL, 0.2 mol) in THF over a period of 45 min ("1.A, Scheme A). After 0.5 hour at −78° C., 3-bromo-2-methylpropene (18.91 mL, 187 mmol) was added dropwise to the orange-yellow suspension. After the addition was complete, the reaction mixture was stirred for an additional 0.5 hour at 0° C. and then allowed to warm to room temperature. After 1 hour the reaction mixture was concentrated under reduced pressure to give an orange-colored oil. The crude material was dissolved in ethyl acetate (EA) (600 mL), washed with brine (100 mL), dried over anhydrous $MgSO_4$ and concentrated under reduced pressure to give the desired compound (60 g, 99%), which was used for the next step without further purification.

$^1$H NMR ($CDCl_3$, 300 MHz), δ 7.1–7.7 (m, 10H), 4.72 (dd, 2H), 4.2 (m, 3H), 2.63 (m, 2H), 1.5 (s, 3H), 1.27 (t, 3H).

B. Ethyl (2RS)-2-Amino-4-methyl-4-pentenoate Hydrochloride

To a stirred solution of the alkylated Schiffs base from EXAMPLE 1.A above (60g, 0.187 mol) in diethyl ether (1.2 L) was added 1 N aqueous HCl (500 mL). The resulting biphasic mixture was stirred for 24 hours at RT. The aqueous layer was separated from the ether layer, washed twice with EA (200 mL) and the aqueous solution was concentrated under reduced pressure to give the desired product "B", Scheme A (36 g, 99%) as viscous oil.

$^1$H NMR ($CDCl_3$, 300 MHz) δ 5.1 (br s, 1H), 4.9 (br s, 1H), 4.32 (m, 3H), 2.5–2.9 (m, 2H), 1.83 (d, 3H), 1.36 (t, 3H).

Scheme B

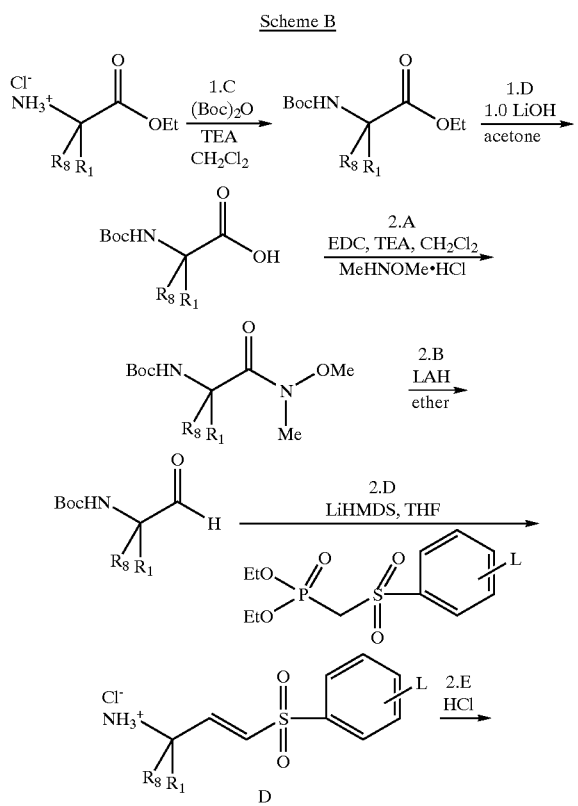

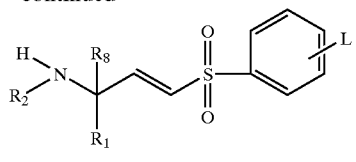

C. Ethyl (2RS)-2-tert-Butoxycarbonylamino-4-methyl-4-pentenoate

To a stiffed solution of ethyl (2RS)-2-amino-4-methyl-4-pentenoate "B", EXAMPLE 1.B, above, (6.0 g, 0.031 mol) in $CH_2Cl_2$ (75 mL) was added di-tert-butyl dicarbonate $(Boc)_2O$; 6.79 g, 0.031 mol) followed by triethylamine (TEA, 8.7 mL, 0.062 mol) and the reaction mixture was left stirred at RT overnight. After overnight, the reaction mixture was diluted with water (100 mL), the organic layer was separated and washed with 0.5 N aqueous HCl (75 mL), water (75 mL, dried over anhydrous $Na_2SO_4$ and concentrated under reduced pressure to give a yellow oil. The resultant crude material was purified via chromatography on silica (hexanes (H):EA, 3:1) to give ethyl (2RS)-2-tert-butoxycarbonylamino-4-methyl4-pentenoate as a colorless oil (6.9 g, 87%).

$^1$H NMR ($CDCl_3$, 300 MHz) δ 4.9 (m, 1H), 4.8 (br s, 1H), 4.7 (br s, 1H), 4.4 (m, 1H), 4.2 (dq, 2H), 2.3–2.6 (m, 2H), 1.7 (s, 3H), 1.42 (s, 9H), 1. 25 (t, 3H).

D. (2RS)-2-tert-Butoxycarbonylamino-4-methyl-4-pentenoic Acid

To a stirred solution of ethyl (2RS)-2-tert-butoxycarbonylamino-4-methyl-4-pentenoate EXAMPLE 1.C, above (6.9 g, 26.9 mmol) in acetone (50 mL was added LiOH (108 mL of 1 N aqueous solution, 108 mmol). The clear solution was stirred at room temperature for 0.5 hour. Acetone was evaporated under reduced pressure, the pH of the resulting aqueous solution was then adjusted to 3 by addition of 1 N HCl and the aqueous layer was extracted with EA (3×50 mL). The organic layers were combined, washed with brine (50 mL), dried over anhydrous $Na_2SO_4$ and concentrated under reduced pressure to give the desired acid as a pale yellow oil in quantitative yield.

$^1$H NMR ($CDCl_3$, 300 MHz) δ 4.95 (m, 1H), 4.9 (br s, 1H), 4.8 (br s, 1H), 4.4 (m, 1H), 2.3–2.7 (m, 2H), 1.76 (s, 3H), 1.55 (s, 9H).

EXAMPLE 2

(3RS)-1-Phenylsulfonyl-3-amino-5-methyl-1E,5-hexadiene Hydrochloride

A. N,O-Dimethyl (2RS)-2-tert-Butoxycarbonylamino-4-methyl-4-pentenoylhydroxamate To a solution of (2RS)-2-tert-butoxycarbonylamino-4-methyl4-pentenoic acid (EXAMPLE 1C; Scheme B) in $CH_2Cl_2$ (50 mL was added 1-(3-dimethyl-aminopropyl)-3-ethyl-carbodiimide hydrochloride (EDC) (5.67 g, 0.296 mol) and NO-dimethylhydroxylamine hydrochloride (MeHNOMe.HCl; 2.89 g, 0.0296 mol). The resulting suspension was cooled to 0° C., TEA (4.12 mL, 0.0296 mol) was added dropwise and the reaction mixture was allowed to warm to room temperature and left stirring overnight. After overnight, the reaction mixture was poured into cold water (75 mL) and extracted three times with $CH_2Cl_2$ (350 mL). The organic layers were combined, washed with 1 N HCl (75 mL), brine (75 mL), dried over $Na_2SO_4$ and concentrated under reduced pressure. The resultant crude product was purified by flash chromatography on silica gel using chloroform/methanol (99:1) as eluant to afford the desired compound (7.33 g, 53%).

$^1$H NMR (CDCl$_3$, 300 MHz) 5.2 (m, 1H), 4.83 (br s, 1H), 4.76 (br s, 1H), 3.8 (s, 3H), 3.2 (s, 3H), 2.1–2.5 (m, 2H), 1.77 (s, 3H), 5 1.4 (s, 9H).

B. (2RS)-2-tert-Butoxycarbonylamino-4-methyl-4-pentenal

Lithium aluminum hydride (LAH, 0.42 g, 11 mmol) was suspended in anhydrous diethyl ether (50 mL). A solution of the Weinreb amide in diethyl ether (10 mL was added dropwise at 0° C. After 0.5 hour at this temperature, the reaction mixture was quenched by sequential addition of water (0.42 mL), 15% aqueous NaOH solution (0.42 mL) and water (1.26 mL). The precipitated inorganic salts were filtered through celite, and the filter pad washed with ether (50 mL). The filtrate was concentrated under reduced pressure to give the aldehyde as a clear viscous oil (3.35 g). The compound was used the same day for the subsequent steps without further purification.

C. Diethyl(Phenylsulfonyl)methylphosphonate

A stirred solution of methyl phenyl sulfone (20 g, 0.128 mol) in dry THF (200 mL) was cooled at −78° C. in an acetone/dry ice bath. Lithium bis(trimethylsilyl)amide (Li HMDS; 134 mL, 1 M solution in THF, 0.134 mol) was added dropwise over 1 h. The resulting white suspension was stirred for an additional hour at −78° C. and diethyl chlorophosphate (18.5 mL, 128 mmol) in THF (20 mL) was added. The reaction mixture was stirred at −78° C. for 0.5 h, then allowed to slowly warm to room temperature and left stirring for 4 h. The reaction mixture was next concentrated under reduced pressure, the residue was dissolved in EA (500 mL), washed with brine (100 mL),dried over anhydrous Na$_2$CO$_3$ and concentrated under reduced pressure. The resultant crude material was purified by flash chromatography on silica gel (EA:H, 3:1 to 1:1) to afford the desired product as white solid (17.9 g, 48%).

$^1$H NMR (CDCl$_3$, 300 MHz) δ 7.5–8.1 (m, 5H), 4.16 (q, 4H), 3.8 (s, 1H), 3.74 (s, 1H), 1.29 (t, 6H).

D. (3RS)-3-tert-Butoxycarbonylamino-5-methyl-1-phenylsulfonyl-1E,5-hexadiene

To a stirred solution of diethyl(phenylsulfonyl) methylphosphonate(from EXAMPLE 2.C) (3.54 g, 0.0121 mol) in dry THF (70 ml) at −78° C. was added slowly a solution of lithium bis(trimethylsilyl)amide (LiHMDS; 13.2 ml, 1 M solution in THF, 13.2 mol) over 0.5 h. The reaction mixture was stirred for another 0.5 h at −78° C., and a solution of crude (2RS)-2-tert-butoxycarbonylamino-4-methyl-4-pentenal from EXAMPLE 2.B (2.35 g, 11.0 mol) in dry THF (20 ml) was added dropwise. After addition was complete, the reaction mixture was stirred for an additional 0.5 hour and then allowed to warm to room temperature and stirred for an additional 3 h. The stirred reaction mixture was concentrated under reduced pressure and the residue was dissolved in EA (100 mL). The EA solution was washed with brine (50 mL), dried over MgSO$_4$ and concentrated under reduced pressure to give an oil. The resultant crude material was purified via flash chromatography on silica gel (H:EA, 6:1) to provide the desired sulfone "D", Scheme B (1.82 g, 47% overall yield for 2.C and 2.D).

$^1$H NMR (CDCl$_3$, 300 MHz) δ 7.9–7.5 (m, 5H), 6.9 (br d, 1H), 6.44 (d, 1H), 4.88 (br s, 1H), 4.76 (br s, 1H), 4.5 (m, 2H), 2.2–2.3 (m, 2H), 1.72 (s, 3H), 1.37 (s, 9H).

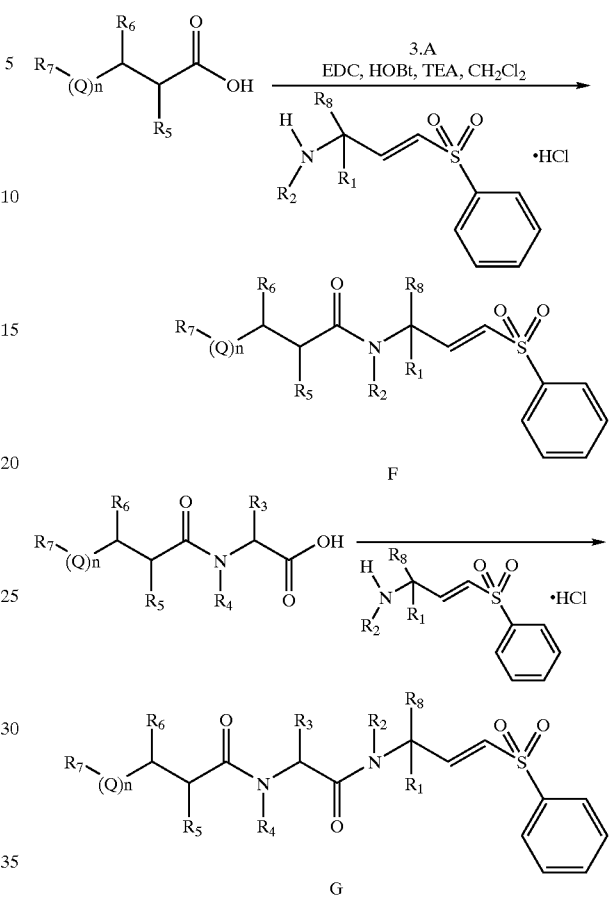

Scheme C

E. (3RS)-1-Phenylsulfonyl-3-amino-5-methyl-1E,5-hexadiene Hydrochloride

To stirred solution of the vinyl sulfone from EXAMPLE 2.D, above (0.75 g, 13 mmol) in CH$_2$Cl$_2$ (10 ml) was added HCl (10.5 mL of a 4 M dioxane solution, 43.0 mol). The reaction mixture was stirred at room temperature for 0.5 h and then concentrated under reduced pressure to provide 0.61 g (99%) of the desired product as a white solid.

$^1$H NMR (CD$_3$OD, 300 MHz) δ 7.92–7.89 (m, 2H), 7.72–7.61 (m, 3H), 7.05–6.83 (m, 2H), 5.02 (br s, 1H), 4.85 (br 5, 1H), 4.21 (q, 1H), 2.6–2.48 (m, 2H), 1.71 (s, 3H).

(3RS)-L-Leu-N-[3-(1-Phenylsulfonyl)-5-methylhexa-1E,5-dieneamide

A. (3RS)-N-Boc-L-Leu-N-[3-(1-Phenylsulfonyl)-5-methylhexa-1E,5-dieneamide

To a stirred solution of N-Boc-Leu-OH (available from Aldrich Chemical Co., Milwaukee, Wis.) (1.66 g, 6.7 mmol) in anhydrous CH$_2$Cl$_2$ (30 mL) at RT were added 1-hydroxybenzotriazole (HOBt) (1.64 g, 12.1 mmol), EDC (1.28 g, 6.7 mmol), (3RS)-1-phenylsulfonyl-3-amino-5-methyl-1E,5-hexadiene hydrochloride from EXAMPLE 2.E (1.74 g, 6.06 mmol) and di-isopropylethylamine (DILA) (0.86 g, 6.7 mmol). The reaction mixture was stirred at room temperature for 17 h and then concentrated under reduced pressure. The residue was resuspended in ethyl acetate (EA) (100 mL, washed successively with saturated bicarbonate solution (50 mL), 10% citric acid (50 mL), and brine (50 mL), dried over anhydrous MgSO$_4$, and concentrated under reduced pressure. The resultant crude product, ("F, Scheme C), was purified by chromatography (EA:H, 1:2) to yield the desired product as colorless oil (2.19 g, 78%).

¹H NMR (CDCl₃, 300 MHz) δ 7.87–7.80 (m, 2H), 7.61–7.48 (m, 3H), 6.9 (dt, 1H), 6.5 (m, 1H), 6.3 (m, 1H), 6.15 (m, 1H), 4.86 (br s, 1H), 4.17 (br s, 1H), 3.9 (m, 1H), 2.2–2.4 (m, 2H), 1.7 (s, 3H), 1.4 (br s, 9H), 0.9 (m, 9H).

B. (3RS)-L-Leu-N-[3-(1-Phenylsulfonyl)-5-methylhexa-1E,5-dieneamide

This compound was prepared following the procedure of EXAMPLE 2.D and 2.E, above using (3RS-3-tert-butyoxycarbonylamino-5-isobutyl-1-phenylsulfonyl-1E,5 hexadiene as a starting material.

¹H NMR (CD₃OD) δ 8.62–8.45 (m, 1H), 7.77–7.70 (m, 2H), 7.58–7.43 (m, 3H), 6.80–6.71 (m, 1H), 6.47–6.42 (m, 1H), 4.67–4.61 (m, 2H), 3.68–3.63 (m, 2H), 2.25–2.00 (m, 2H), 1.56–1.44 (s overlaps m, 6H), 0.79 (d, 6H).

EXAMPLE 4

(3RS)-N-Cbz-L-Val-L-Leu-N-[3-(1-Phenylsulfonyl)-5-methyl-hexa-1E,5-dieneamide

The title compound was prepared from N—Cbz-L-Val-OH (available from Bachem) and (3RS)-L-Leu-N-[3-(1-phenylsulfonyl)-5-methylenehexa-1E,5-dien]amide (EXAMPLE 3) using substantially the same procedure as described in EXAMPLE 3 to isolate the desired product as a colorless oil (10 mg).

¹H NMR (CDCl₃, 300 MHz) δ 7.89–7.83 (m, 2H), 7.60–7.5 (m, 3H), 7.34–7.35 (m, 5H), 6.92 (dd, 1H), 6.56–6.51 (m, 1H), 6.36 (m, 1H), 5.32 (m, 1H), 5.13–5.10 (m, 3H), 4.85–4.75 (m, 3H), 4.45 (m, 1H), 3.93 (m, 1H), 2.35–2.10 (m, 2H), 1.73–1.47 (m, 7H), 0.97–0.84 (m, 12H).

EXAMPLE 5

(3RS)-N-Cbz-L-Leu-L-Met-N-[3-O-Phenylsulfonyl)-5-methylhexa-1E,5-dieneamide

The title compound was prepared from N-Cbz-L-Leu-L-Met-OH synthesized by solid phase peptide synthesis (or purchased from Bachem) and using (3RS)-1-phenylsulfonyl-3-amino-5-methyl-1E,5-hexadiene hydrochloride (EXAMPLE 2.E) as a starting material in substantially the same procedure described in EXAMPLE 3 (Scheme C). The product was isolated as a colorless oil (10 mg).

¹H NMR (CDCl₃, 300 MHz) δ 7.89–7.83 (m, 2H), 7.60–7.47 (m, 3H), 7.37–7.33 (m, 5H), 6.97–6.90 (m, 2H), 6.5 (m, 1H), 5.28–5.23 (m, 4H), 5.14–5.07 (M, 3H), 4.52 (m, 1H), 4.1 (m, 1H), 2.5–1.64 (m overlaps s, 15H), 0.92 (m, 6H).

EXAMPLE 6

(2S)-2-tert-Butoxycarbonylamino-4-methyl-4-pentenoic Acid

A. (2S)-2-Amino-4-methyl-4-pentenoyl (S,S)-Pseudoephedrine Amide

To a suspension of dry LiCl (4.2 g, 99 mmol) in dry THF (45 mL was added diisopropylamine (DIA, 4.6 mL, 32.8 mmol). The flask was cooled to −78° C. in a dry ice/acetone bath and a solution of n-BuLi (hexanes, 12.7 mL, 31.8 mmol) was added in drops. The solution was stirred for 10 minutes, then a solution of

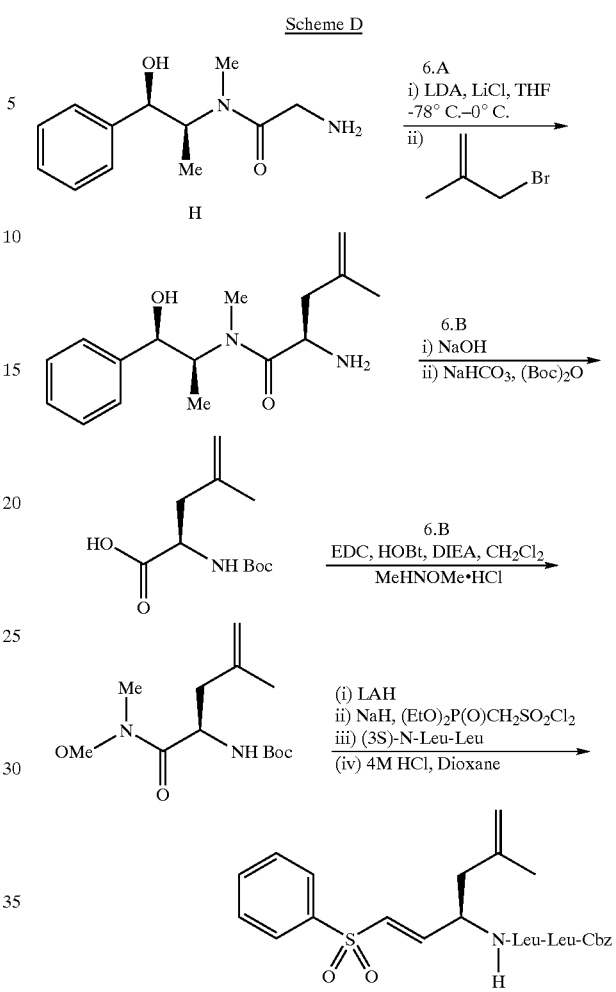

Scheme D (S,S)-pseudoephedrine glycinamide ("H", Scheme D; prepared according to Myers et al. *J. Am. Chem. Soc.* 117: 8488–8489, 1995) (3.6 g, 16.3 mmol) in THF (25 mL) was added in drops over a period of 10 minutes. The reaction mixture was left stirring at −78° C. for 20 minutes, changed to an ice bath and stirred at 0° C. for 20 min. 3-Bromo-2-methylpropene (1.8 ml, 17.8 mmol) was added dropwise to the reaction mixture. After 0.5 h, 1.0 N HCl (110 mL) was added followed by EA (150 mL). The aqueous layer was separated and the EA solution was extracted with 1.0 N HCl (110 mL). The combined HCl solution was cooled in an ice bath and the pH adjusted to pH 14 using 50% NaOH. The basic solution was extracted twice with CH₂Cl₂ (80 ml each) and the combined CH₂Cl₂ solutions were dried over anhydrous K₂CO₃, filtered and concentrated to give a colorless oil that was purified by flash chromatography on silica gel (5% MeOH in CH₂Cl₂) to give a colorless oil (2.95 g, 66%).

¹H NMR (CDCl₃, 300 MHz) (mixture of rotomers) δ 7.38–7.27 (m, 5H), 4.94–4.78 (m, 2H), 4.65–4.46 (m, 2H), 3.91–3.87 (dd, 0.2H) 3.79–3.74 (dd, 0.8H), (m, 1H), 3.11–2.98 (br, 1H), 2.97 (s, 0.6H), 2.89 (s, 2.4H), 2.22–1.74 (m overlaps s, 7H), 1.12–1.09 (dd, 2.4H), 1.01–1.08 (d, 0.6H).

B. (2S)-2-tert-Butoxycarbonylamino-4-methyl-4-pentenoic Acid

To an aqueous solution of 1.0 N NaOH (15.2 ml, 15.2 mmol) was added a solution of (2S)-2-amino-4-methyl-4-pentenoyl (S,S)-pseudoephedrine amide (EXAMPLE 6.A, above) (2.03 g, 7.6 mmol) in water (15.2 mL). The reaction mixture was stirred under reflux for 1.5 h, and cooled to RT. The crystallized pseudoephedrine was filtered, and the filtrate was diluted with water (75 mL). The aqueous solution was extracted twice with $CH_2Cl_2$ (150 mL). The combined $CH_2Cl_2$ solutions were extracted with water (100 mL) and the aqueous solution was washed with $CH_2Cl_2$ (75 mL). The aqueous solutions were then combined and concentrated under reduced pressure, about 50 mL, solid $NaHCO_3$ (1.49 g) was added to this aqueous solution followed by p-dioxane (55 mL). The resulting solution was cooled to 0° C. and di-tert-butyl dicarbonate ($Boc_2O$; 2.0 g, 9.17 mmol) was added. The reaction was left stirring at 0° C. for 1 h, and the temperature was warmed to room temperature and stirred for an additional 0.5 h. The reaction mixture was diluted with water (150 mL) and extracted with EA (i.e., DIEA; 150 mL). The EA solution was re-extracted with 2% $NaHCO_3$ (100 mL) solution. The combined bicarbonate solutions were then acidified to pH 3 using 10% citric acid solution. The acidic solution was extracted three times with EA (100 mL). The combined EA solutions were washed with water (2 times; 100 mL each), dried with $MgSO_4$ filtered and concentrated to give 1.46 g (84%) of product as colorless oil.

$^1$H NMR ($CDCl_3$, 300 MHz) δ 9.8 (br, 1H), 5.3–4.80 (m, 3H), 4.34–4.31 (m, 2H), 2.62–2.56 (m, 2H), 1.76 (s, 3H), 1.43 (s, 9H).

EXAMPLE 7

(3S)-N-Cbz-L-Leu-L-Leu-N-[3-(1-Phenylsulfonyl)-5-methylhexa-1E,5-dieneamide

N-Cbz-L-Leu-L-Leu (Bachem), the (2S)-2-tert-butoxycarbonylamino-4-methyl-4-pentenoic acid product of EXAMPLE 6.B and diethyl-(phenylsulfonyl)-methylphosphonate (EXAMPLE 2.C) were combined using the procedure of EXAMPLES 2 and 3, above, to provide the title compound as a colorless oil.

$^1$H NMR ($CDCl_3$, 300 MHz) δ 7.86–7.83 (m, 2H), 7.59–7.46 (m, 2H), 7.41–7.29 (m, 5H), 6.95–6.90 (dd, J=3.9, 11 Hz, 1H), 6.79–6.66 (br d, J=3.9 Hz, 1H), 6.59–6.56 (m, 2H), 5.46–5.44 (br m, J=6.9 Hz, 1H), 5.14–4.99 (AB q, J=12.3 Hz, 2H), 4.84–4.72 (m, 3H), 4.38–4.34 (m, 1H), 4.13–4.09 (m, 1H), 2.30–2.03 (m, 2H), 1.67 (s, 3H), 1.64–1.25 (m, 6H), 0.89–0.81 (overlapping doublets, 12H).

EXAMPLE 8

(3R)-N-Cbz-L-Leu-L-Leu-N-[3-(1-Phenylsulfonyl)-5-methylhexa-1E,5-dieneamide

The title compound was prepared according to the procedure set forth in EXAMPLE 7, using (2R)-2-tert-butoxycarbonylamino-4-methyl-4-pentenoic acid in place of (2S)-2-tert-butoxycarbonylamino-4-methyl-4-pentenoic acid, to afford the desired product as a colorless oil. (2R)-2tert- Butoxycarbonylamino-4-methyl-4-pentenoic acid was prepared according to EXAMPLE 6, above, using (R,R)-pseudoephedrine glycinamide.

EXAMPLE 9

(3RS)-4-Benzylpiperidinocarbonyl-L-Leu-L-Leu-N-[3-(1-phenylsulfonyl)-5-methylhexa-1E,5-dienelamide

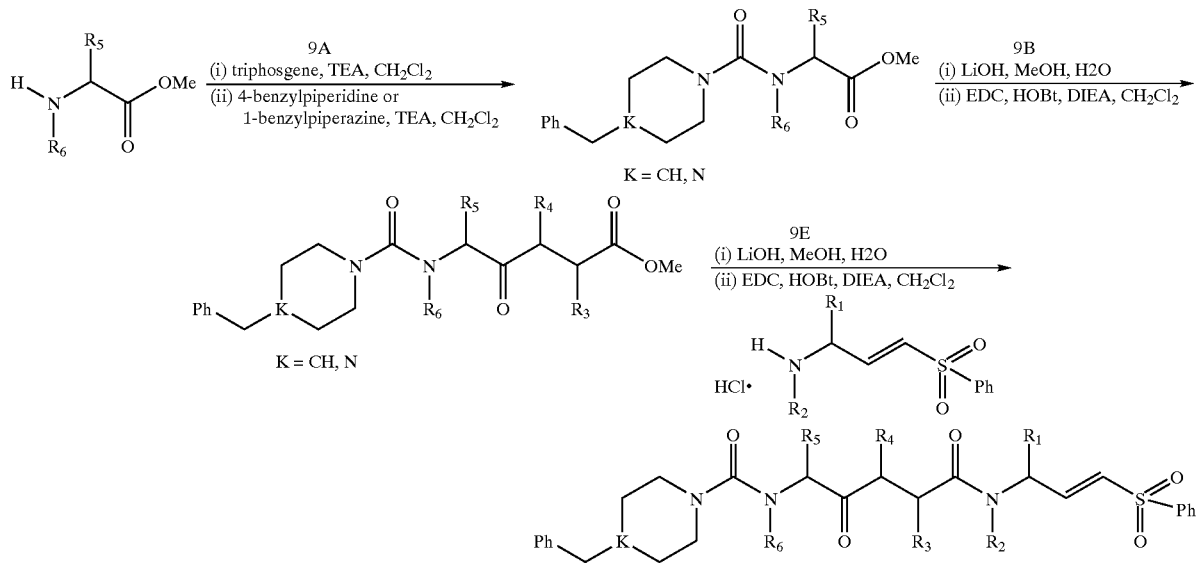

Scheme E

K = CH, N

A. 4-Benzylpiperidinocarbonyl-L-Leu-OMe

To a stirred solution of triphosgene (1.02 g, 3.4 mmol) in anhydrous $CH_2Cl_2$ (50 mL) was added a solution of L-Leu-OMe (available from Aldrich Chemical Co., Milwaukee, Wis.) (1.8 g, 10.3 mmol) and TEA (1.43 ml, 10.3 mmol) in $CH_2Cl_2$ (25 mL) dropwise over a period of 15 min. (Scheme E). The reaction mixture was stirred at room temperature for 3 h and then a solution of 4-benzylpiperidine (1.81 ml, 10.3 mmol) and TEA (1.45 mL in anhydrous $CH_2Cl_2$ (25 mL) was added in dropwise. The reaction mixture was then stirred at room temperature for 12 h, concentrated under reduced pressure. The residue was re-dissolved in EA (100 mL) and was washed successively with saturated bicarbonate (50 mL), brine (50 mL), 1.0 N HCl (50 mL) and saturated brine (50 mL), dried over anhydrous $MgSO_4$ filtered and concentrated to give a colorless oil that was purified by silica gel chromatography (2% $MeOH:CH_2Cl_2$) to yield the desired product as a colorless oil (2.6 g, 73%).

$^1$H NMR ($CDCl_3$, 300 MHz) δ 7.24–7.05 (m, 5H), 4.81–4.78 (d, J=5.1 Hz, 1H), 4.46–4.39 (m, 1H), 3.91–3.83

(m, 2H), 3.63 (s, 3H), 2.71–2.59 (m, 2H), 2.48–2.46 (d, 2H), 1.65–1.40 (m, 6H), 1.18–1.08 (m, 2H), 0.88–0.86 (d, 6H).

B. 4-Benzylpiperidinocarbonyl-L-Leu-OH

A solution of 4-benzylpiperidinocarbonyl-L-Leu-OMe (EXAMPLE 9.A., above) (2.6 g, 7.5 mmol) in MeOH (60 ml) was cooled to 0° C., LiOH:H₂O (1.26 g, 30 mmol) in water (20 mL) was added and the reaction mixture was stirred at 0° C. for 2 h and at room temperature for 12 h (Scheme E). The reaction mixture was then concentrated under reduce pressure to 30 ml, diluted with EA (100 ml) and the EA solution was acidified with 1.0 N HCl to pH 1. The organic layer was separated and the aqueous layer was extracted with EA (50 mL). The combined EA solutions were washed with water (2 time; 50 mL), dried over anhydrous MgSO₄ filtered and concentrated under reduced pressure to give the desired product as a colorless oil (2.5 g, 99%).

¹H NMR (CDCl₃, 300 MHz) 7.32–7.11 (m, 5H), 5.26–5.23 (d, 1H), 4.53–4.48 (m, 1H), 3.94–3.89 (m, 2H), 2.74–2.66 (br t, 2H), 2.54–2.52 (d, 2H), 1.86–1.52 (m, 6H), 1.32–1.22 (m, 2H), 0.93 (d, 6H).

C. 4-Benzylpiperidinocarbonyl-L-Leu-L-Leu-OMe

The title compound was prepared using the procedure set forth in EXAMPLE 9.A, above, using Leu-Leu-OMe as a starting material instead of Leu-OMe. The product was isolated as a colorless oil (332 mg, 69%).

¹H NMR (CDCl₃, 300 MHz) δ 7.48–7.1 (m, 5H), 5.28–5.21 (br d, 1H), 4.61–4.40 (m, 2H), 3.94–3.82 (m, 2H), 2.71 (t, 2H), 2.76 (d, 2H), 1.90–1.69 (m, 9H), 1.48–1.34 (m, 2H), 1.17–1.12 (m, 12H).

D. 4-Benzylpiperdinocarbonyl-L-Leu-L-Leu-OH

The title compound was prepared as a colorless oil from the product of 9.C using the procedure of EXAMPLE 9.B.

¹H NMR (CDCl₃, 300 MHz) δ 7.34–7.11 (m, 5H), 5.24 (d, 1H), 4.61–4.48 (m, 3H), 3.94–3.90 (br m, 2H), 2.70 (br t, 2H), 2.53 (d, 2H), 1.71–1.59 (m, 9H), 1.24–1.10 (m, 2H), 0.96–0.88 (m, 12H).

E. (3RS)-4-Benzylpiperidinocarbonyl-L-Leu-L-Leu-N-[3-(1-phenylsulfonyl)-5-methylhexa-1E,5-dieneamide To a stirred solution of 4-benzylpiperidinocarbonyl-L-Leu-L-Leu-OH (138 mg, 0.31 mmol) in 3 mL of anhydrous CH₂Cl₂ at room temperature was added HOBt (42 mg, 0.31 mmol), EDC (65 mg, 0.34 mmol), DIEA (107 mL, 0.62 mmol) and 3(RS)-1-phenylsulfonyl-3-amino-5-methyl-1E,5-hexadiene hydrochloride from EXAMPLE 2.E (Scheme E). The reaction mixture was stirred at room temperature for 12 h, diluted with 50 mL of EA, washed with 50 mL of saturated bicarbonate solution, 10% citric acid and water, dried with MgSO₄, filtered and concentrated to give crude product that was purified by silica gel chromatography (3% MeOH in CH₂Cl₂) to yield 170 mg (81%) of product as white foamy solid. ¹H NMR (CDCl₃, 300 MHz) δ 7.89–7.79 (m, 2H), 7.61–7.45 (m, 3H), 7.31–7.11 (m, 5H), 6.95–6.87 (m, 1H), 6.76–6.72 (m, 1H), 6.61–6.48 (m, 1H), 4.96 (d, 1H), 4.87–4.65 (m, 3H), 4.35–4.25 (m, 1H), 4.16–3.80 (m, 3H), 2.87–2.85 (m, 2H), 2.65 (d, 302H), 2.36–2.20 (m, 3H), 1.79–1.40 (m, 12H), 1.21–1.07 (m, 2H), 0.90–0.79 (m, 12H).

EXAMPLE 10

(3RS)-Tetrahydroisoquinolinylcarbonyl-L-Leu-L-Leu-N-[3-0-phenylsulfonyl)-5-methy[hexa-1E,5-dieneamide The title compound was obtained as a glassy solid following the procedure described in EXAMPLE 9.A and 9.B, above, but using 1,2,3,4-tetrahydroisoquinoline as a reagent instead of 4-benzylpiperidine (Scheme F).

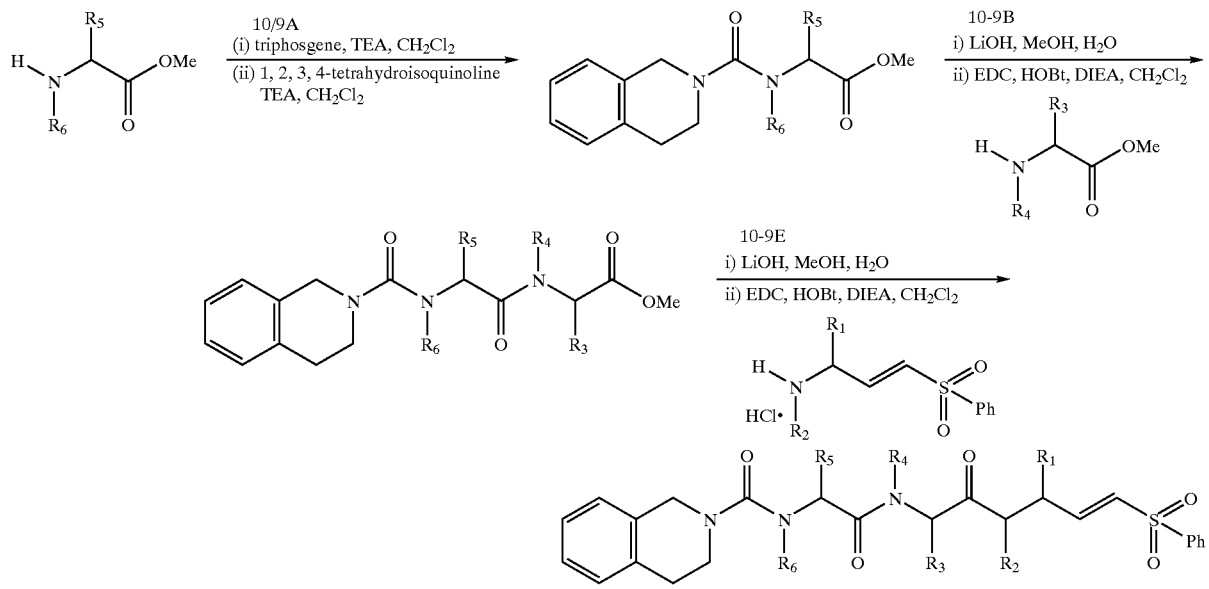

¹H NMR (CDCl₃, 300 MHz) δ 7.85–7.83 (d, 2H), 7.57–7.44 (m, 3H), 7.27–7.13 (m, 5H), 6.96–6.89 (dd, 1H), 6.85–6.83 (d, 1H), 6.60–6.54 (dd, 1H), 5.01 (d, 1H), 4.84–4.73 (m, 3H), 4.63–4.46 (q, 2H), 4.36–4.28 (m, 1H), 4.24–4.18 (m, 1H), 3.69–3.47 (m, 2H), 2.89–2.84 (m, 2H), 1.74–1.72 (d, J=5.1 Hz, 2H) 1.70 (s, 3H), 1.74–1.46 (m, 6H), 0.97–0.89 (overlapping doublets, 12H).

EXAMPLE 11

(3RS)-Tetrahydroisoquinolinylcarbonyl-L-Val-L-Met-N-[3-(1-phenylsulfonyl)-5-methylhexa-1E,5-dieneamide The title compound was isolated as a colorless oil (100 mg) following the procedure outlined in EXAMPLE 10 (Scheme F), but using L-Val-OMe and L-Met-OMe as reagents (both available from Aldrich Chemical Co., Milwaukee, Wis.) instead of L-Leu-OMe.

$^1$H NMR (CDCl$_3$, 300 MHz) δ 7.85–7.80 (m, 2H), 7.60–7.40 (m, 3H), 7.19–7.12 (m, 5H), 6.75 (dd, 1H), 6.43–6.32 (m, 1H), 5.14–4.44 (m, 8H), 3.97–3.92 (m, 1H), 3.70–3.50 (m, 2H), 2.87–2.84 (m, 2H), 2.5–1.95 (m, overlaps s, 10H), 1.7 (s, 3H), 0.98–0.83 (m, 6H).

EXAMPLE 12

(3RS)-Tetrahydroisoquinolinylcarbonyl-L-Val-L-Leu-N-[3-(1-phenylsulfonyl)-5-methylhexa-1E,5-dienelamide The title compound was isolated as a color less oil (50 mg) following the procedure outlined in EXAMPLE 10 (Scheme F), above, but using L-Leu-OMe as a reagent in place of L-Met-OMe.

$^1$H NMR (CDCl$_3$, 300 MHz) δ 7.82–7.7 (m, 2H), 7.55–7.45 (m, 3H), 7.22–7.12 (m, 4H), 7.09–7.01 (m, 1H), 6.95–6.93 (m, 1H), 6.62–6.12 (m, 2H), 5.14–4.49 (m, 6H), 4.36–4.20 (m, 1H), 4.0–3.92 (m, 1H), 3.71–3.53 (m, 2H), 2.97–2.85 (m, 2H), 2.49–2.02 (m, 3H), 1.64–1.24 (m overlaps s, 6H), 1.0–0.81 (m, 12H).

EXAMPLE 13

(3S)-4-N-Benzylpiperazinylcarbonyl-L-Leu-L-Leu-N-[3-(1-phenylsulfonyl)hexamide

Following the procedure set forth in EXAMPLE 9 (Scheme D), above, substituting 1-benzylpiperazine for 4-benzylpiperidine and substituting (3S)-1-phenylsulfonyl-3-amino-5-methyl-1E,5-hexadiene hydrochloride (e.g., prepared in a manner similar to that set forth in EXAMPLE 7) for (3RS)-1-phenylsulfonyl-3-amino-5-methyl-1E,5-hexadiene hydrochloride. The title compound was isolated as a colorless oil.

$^1$H NMR (CD$_3$OD, 300 MHz) δ 7.79–7.77 (m, 2H), 7.60–7.46 (m, 3H), 7.24–7.16 (m, 5H), 6.84–6.77 (dd, J=5.1, 15 Hz, 1H), 6.55–6.49 (dd, J=1.5, 15 Hz, 1H), 4.46–4.43 (m, 1H), 4.21–4.17 (m, 1H), 4.05–4.00 (m, 1H), 3.40–3.20 (m, 6H), 2.35–2.32 (m, 4H), 1.62–1.39 (m, 8H), 1.23–1.19 (m, 4H), 0.88–0.77 (m, 15H).

EXAMPLE 14

Illustrative In Vitro Assays

Summary Overview: Illustrative methods are described above by which the instant compounds may be synthesized. Testing the intracellular effects of a compound may be accomplished according to cell-based methods disclosed herein, such as those illustrated below using cultured human glioblastoma (HGB) cells stably-transfected with cDNA constructs encoding APP, e.g., the 695 amino acid β-amyloid precursor protein (APP$_{695}$), as well as other possible truncated forms of APP.

Cell-Based Screening Assays: An in vitro system may be used to assay the instant compounds and confirm those that modulate APP:Aβ processing. For instance, the human glioblastoma (HGB) cell line normally secretes only soluble derivatives of APP$_{751}$, but APP:Aβ processing may be altered to resemble processing in Alzheimer's disease by stable transfecting the HGB cells with a cDNA construct encoding either: (i) a wild-type 695 amino acid APP (APP$_{695wt}$), or (ii) a 695 amino acid APP containing a "Swedish" double mutation with Asn for Lys and Leu for Met substitutions at codons 670 and 671, respectively, (APP$_{670/671}$), (codons numbered according to the 770 amino acid APP isoform), or (iii) a 695 amino acid APP containing the 670/671 double mutation and a Phe for Val substitution at codon 717 (APP$_{670/671/717}$). Altered APP:Aβ processing in the HGB cells may e.g. by determined by collecting conditioned medium from the stably transfected cells and immunobloting with monoclonal antibody specific for an N-terminal sequence in APP (e.g., mAb22C1), and/or a monoclonal antibody specific for the amino terminus of Aβ (e.g. mAb6E10). One or more of the instant compounds are added to the transfected/altered HGB cells and APP:Aβ processing determined by immunobloting with comparison being made between cell cultures, so treated, and untreated control cultures, i.e., using medium collected from the cell cultures and/or cell extracts.

M-17 neuroblastoma cells transfected with a mutant APP construct (APP$_{695NL+1}$) secrete high levels of Aβ and a significant fraction is AP$_{1-42}$ (39). HGB cells stably-transfected with a construct encoding APP 670/671/717 or APP$_{695NL+F}$ will secrete detectable levels of an ~4 kD peptide, i.e., AP$_{1-40}$ detectable by immunoprecipitations, SDS-PAGE and/or western blotting. The ability of the instant compounds to modulate APP:Aβ processing in these cells is detected by evaluating Aβ levels in the medium collected from cell cultures or in cell culture extracts.

Quantitative assays for Aβ can be used to measure the levels of APP processing to Aβ, both in vitro e.g., in one or more of the cell-based assays, above, and also in extracts of animal tissues or in primary cultures of mixed brain cells (termed mixed brain cultures). For example, immunoblotting of SDS-PAGE gels with polyclonal rabbit anti-APP$_{645-697}$ (i.e., R$_{369}$) may used to reveal the different molecular weight species of APP antigens in tissues. Immunoblotting with monoclonal antibody 26D6, specific for amino acid residues 1–12 of Aβ$_{1-40}$, may be used to confirm the presence of Aβ in the tissue extracts. Materials and Methods are set forth following the EXAMPLES section, below.

Using such cell-based assays the following results are recorded in vitro:

1. Examples of the instant compounds according to FORMULAS I, II and/or III, above, decrease processing of APP to Aβ in vitro, i.e., as judged by decreased levels of Aβ in treated HGB cell extracts by ELISA, immunoprecipitation and SDS-PAGE and/or western blotting (TABLE I, next page);

2. The instant compound inhibit Aβ formation in vitro in HGB cells without altering the amount of non-APP proteins (e.g., fibronectin, fodrin etc.) synthesized, i.e., as judged by $^{35}$S-biosynthetically radiolabeling proteins synthesized by cells on SDS-PAGE and autoradiography; and 3. The instant compounds inhibited certain cell free cysteinyl proteases in vitro, including Cathepsin S, Calpain I, papain, Cathepsin L, but not Chymotrypsin, Cathepsin H, Cathepsin B or Cathepsin C (TABLE II, below).

TABLE I

Inhibition of APP Processing to Aβ*

| CMPD/Formula[a] | $R_7$ | Q | n | $R_6$ | $R_5$ | $R_4$ | $R_3$ | $R_2$ | $R_1$ | $R_8$ | X | Y | Z | | Aβ Inh. |
|---|---|---|---|---|---|---|---|---|---|---|---|---|---|---|---|
| 1/I | benzyl | —COC(O)— | 1 | H | $(CH_3)_2C$— | H | indolyl | H | iso-butenyl | H | —C≡C— | —S(O)$_2$— | phenyl | | 4+ |
| 2/I | piperidinyl-benzyl- | —C(O)— | 1 | H | $(CH_3)_2C$— | H | $(CH_3)_2C$ | H | iso-butenyl | H | —C≡C— | —S(O)$_2$— | phenyl | | 5+ |
| 3/I | piperidinyl-benzyl- | —C(O)— | 1 | H | $(CH_3)_2C$— | H | $(CH_3)_2C$ | H | butyl | H | —C≡C— | —S(O)$_2$— | phenyl | | 1+ |
| 4/I | benzyl- | —COC(O)— | 1 | H | $(CH_3)_2C$— | H | $(CH_3)_2C$ | H | iso-butenyl | H | —C≡C— | —S(O)$_2$— | phenyl | | 6+ |
| 5/I | benzyl- | —COC(O)— | 1 | H | $(CH_3)_2C$— | H | $(CH_3)_2C$ | H | butyl | H | —C≡C— | —S(O)$_2$— | phenyl | | 2+ |
| 6/I | $(CH_3)_3C$— | —OC(O)— | 1 | $CH_3$ | $(CH_3)_2C$— | H | $(CH_3)_2C$ | H | iso-butenyl | H | —C≡C— | —S(O)$_2$— | phenyl | | 2+ |
| 7/I | $(CH_3)_3C$— | —OC(O)— | 1 | $CH_3$ | benzyl-$CH_2$— | H | $(CH_3)_2C$ | H | iso-butenyl | H | —C≡C— | —S(O)$_2$— | phenyl | | 2+ |
| 8/I | benzyl | —COC(O)— | 1 | H | $CH_3$— | H | $(CH_3)_2C$ | H | iso-butenyl | H | —C≡C— | —S(O)$_2$— | phenyl | | 2+ |
| 9/I | piperidinyl- | —C(O)— | 1 | H | $(CH_3)_2C$— | H | $(CH_3)_2C$ | H | iso-butenyl | H | —C≡C— | —S(O)$_2$— | phenyl | | 7+ |
| 10/I | benzyl- | —COC(O)— | 1 | H | $(CH_3)_2C$— | H | $(CH_2)_2SCH_3$ | H | iso-butenyl | H | —C≡C— | —S(O)$_2$— | phenyl | | 8+ |
| 11/I | benzyl- | —COC(O)— | 1 | H | $(CH_3)_2C$— | H | $(CH_3)_2C$— | H | butyl | H | —C≡C— | —S(O)$_2$— | —$CH_3$ | | 9+ |
| 12/I | benzyl- | —COC(O)— | 1 | H | $(CH_3)_2C$— | H | $(CH_3)_2C$— | H | iso-butenyl | H | —C≡C— | —S(O)$_2$— | phenyl | | 11+ |
| 13/I | benzyl- | —COC(O)— | 1 | H | $(CH)_2C$— | H | $(CH_3)_2C$— | H | iso-butenyl | H | —C≡C— | —S(O)$_2$- benzyl | ethynyol | | 3+ |
| 14/I | benzyl- | —COC(O)— | 1 | H | $(CH_3)_2C$— | H | $(CH_3)_2C$— | H | iso-butenyl | H | —C≡C— | —S(O)$_2$— | phenyl | | 3+ |
| 15/I | benzyl-$CH_2$-piperazinyl | —C(O)— | 1 | H | $(CH_3)_2C$— | H | $(CH_2)_2SCH_3$ | H | iso-butenyl | H | —C≡C— | —S(O)$_2$— | phenyl | | 3+ |
| 16/I | benzyl | —COC(O)— | 1 | H | $(CH_3)_2C$— | H | $(CH_3)_2C$— | $CH_3$ | iso-butenyl | H | —C≡C— | —S(O)$_2$— | phenyl | | 3+ |
| 17/I | benzyl-piperidinyl | —C(O)— | 1 | H | $(CH_3)_2C$— | H | $(CH_3)_2C$— | H | iso-butenyl | H | —C≡C— | —S(O)$_2$— | phenyl | | 3+ |
| 18/I | benzyl-piperidinyl | —C(O)— | 1 | H | $(CH_3)_2C$— | H | $(CH_2)_2SCH_3$ | H | iso-butenyl | H | —C≡C— | —S(O)$_2$— | phenyl | | 3+ |
| 19/I | benzyl | —COC(O)— | 1 | H | $(CH_3)_2C$— | H | $(CH_3)_2C$— | H | iso-butenyl | H | —C≡C— | —S(O)$_2$— | phenyl | | 12+ |
| 20/I | benzyl-$CH_2$-piperidinyl | —C(O)— | 1 | H | $(CH_3)_2C$— | H | $(CH_3)_2C$— | H | iso-butenyl | H | —C≡C— | —S(O)$_2$— | phenyl | | 13+ |

[a]Form.= FORMULA I, II or III, supra;
*Inhibition of APP processing to Aβ determined according to the ELISA methods, Materials and Methods.

TABLE II

Inhibition of Protease Activity In Vitro*

| CMPD[a] | CatS | CatL | Calpain I | Papain | CatB | CatC | CatH | Chymo. |
|---|---|---|---|---|---|---|---|---|
| 1 | ND | 3+ | – | 4+ | – | – | – | – |
| 2 | ND | – | 2+ | – | – | – | – | – |
| 4 | ND | 4+ | – | 4+ | – | – | – | – |
| 5 | ND | – | 2+ | 1+ | – | – | – | – |
| 8 | ND | 4+ | 1+ | 1+ | – | – | ND | – |
| 9 | 4+ | – | 3+ | – | – | – | – | – |
| 10 | ND | 3+ | – | 4+ | – | – | – | – |
| 12 | – | – | – | – | – | – | – | – |
| 14 | 4+ | 4+ | 2+ | – | – | – | ND | – |
| 20 | 4+ | ND | ND | ND | ND | ND | ND | ND |

*Fluorescent and/or colorimetric substrate assays using peptidyl substrates;
ND not determined;
Cat cathepsin,
Chymo. chymotrypsin;
[a]CMPD, compounds as recited in TABLE I, above.

EXAMPLE 15

Illustrative Results in Transgenic Animal Models

Several useful transgenic animal test models of Alzheimer's disease have been described, e.g. Tg2576 and APP-YAC transgenic mice. These animal models are useful for determining the modulatory effects of the instant compounds on APP processing to Aβ. For example, the levels of inhibition of Aβ production in vivo may be determined by measuring the levels of Aβ in brain tissue, CSF fluid or plasma using an ELISA, immunoprecipitation and SDS-PAGE and/or western immunoblot analyses.

Similarly, using APP-YAC homozygous transgenic mice, the instant compounds may be tested to determine whether they inhibit Aβ production. Using such assays the following results may be obtained: namely, 1. The instant compounds perferably inhibit Aβ production as judged by decreased plasma or brain tissue levels of Aβ after administration of a test dose of one of the instant compounds; and, 2. The instant compounds preferably inhibit Aβ production in brain tissues after administration, i.e., as judged by decreased levels of biosynthetically radiolabeled Aβ in immunoprecipitates from brain tissues.

Materials and Methods

Cell Lines: The $HGB_{695wt}$ cell line may be prepared by stably-transfecting human glioblastoma (U138 MG) cells with an $APP_{695}$ expression plasmid. A human neuroblastoma cell line (IMR-32) is potentially useful as the source for mRNA encoding the sequence of $APP_{695}$.

$APP_{695}$ cDNA and plasmids: cDNA encoding the $APP_{695}$ may be derived from mRNA purified from human neuroblastoma cell line (IMR-32), e.g., by RT-PCR amplification followed by cloning into a retroviral construct. The DNA fragment containing the $APP_{695}$ sequence may be removed from a selected cloned retroviral construct, e.g., by partial digestion with endonuclease, and ligated into a mammalian expression vector (e.g. obtained from Invitrogen, Inc., San Diego, Calif.)

Aβ Cells: Transfection of HGB (or other) cells with the $APP_{695}$ cDNA (above) may be accomplished using the Lipofectin kit followed by selection of transformant clones in G418-containing medium.

APP Cells: An expression plasmid construct containing $APP_{695}$ cDNA may be mutated using site-directed mutagenesis in conjunction with PCR to generate an $APP_{695}$ plasmid containing missense mutations. This approach has been used by others to yield $APP_{695}$ coding region mutations, e.g., at codons 670, 671 and 717 (codon numbering based upon the $APP_{770}$ isoform numbering system), where it has proved useful to generate Asn for Lys, Leu for Met and Phe for Val substitutions, respectively. Resulting constructs of this type, e.g. $APP_{670,671,717}$ may be useful for selecting stably-transfect cell lines. Stable cell populations may be subcloned; characterized for expression of exogenous $APP_{695}$ by immunoblotting with APP specific antibodies; and then selected for use in one or more cell-based assays.

Antibodies: The mouse monoclonal antibody, 26D6, anti-human $Aβ_{1-12}$ was prepared by TSD Bioservices. 26D6 IgG, i.e, specific for the N-terminus of Aβ, i.e., $Aβ_{1-12}$, was purified from ascites by affinity purification on Protein A-Sepharose (Pharmacia) chromatography followed by affinity chromatography on an affinity matrix, (i.e., CnBr-activated Sepharose), containing bound $Aβ_{1-12}$, i.e., at an input concentration of 1 mg/ml resin. Affinity purified 26D6 was coupled to horse-radish peroxidase (HRP) by Taconic Bioservices (Newark, Del.). Rabbit antiserum, i.e., R6257, was raised to $APP_{657-676}$.

ELISA for Aβ: An Aβ sandwich ELISA was developed using polyclonal rabbit anti-$Aβ_{1-40}$ as a selective capture antibody and HRP-conjugated monoclonal 26D6 (i.e., mouse monoclonal IgG specific for the N-terminus of Aβ, i.e., $AP_{1-12}$,) for the detect reagent. To measure intracellular levels of Aβ and APP, lysates of $HGB_{695wt}$ cells may be prepared, separated by 16% Novex gradient gels, and immunoblotted with R369, (i.e., rabbit CTF-specific antisera), or the 26D6 monoclonal antibody.

For example, APP α- and β-secretase carboxy-terminal products (iα-CTF and iβ-CTF) may be immunoprecipitated with anti-CTF antisera (and Protein A or Protein G Sepharose), immunoprecipitates can be separated by SDS-PAGE, then Aβ detected by western blotting with quantification being achieved using laser scanning densitometry.

For detection of Aβ in plasma and CSF, an ELISA assay may be used, e.g., using mouse monoclonal IgG anti-$AP_{1-40}$ as a capture antibody and biotinylated mouse monoclonal antibody 4G8 (i.e., anti-$Aβ_{17-24}$) as a detect reagent. After washing to remove unbound detect reagent, avidin-HRP is added to generate a colorometric signal in the assay.

Treatment Studies and Immunochemical Assays In Vitro: Identical confluent cultures of stably-transfected $APP_{695wt}$ or $APP_{670/671/717}$ cells (approximately $10^7$ cells/plate) can be established in 100 $mm^2$ culture dishes and washed with 5 ml of Ultraculture medium. Compounds of interest can be dissolved, e.g., in DMSO, and then diluted using medium. As a control, plates can be treated with medium and diluted DMSO vehicle. After about 16 h incubation at 37° C. with test compound or vehicle, conditioned medium can be collected and clarified, e.g., by low speed centrifugation (1000×g). Clarified conditioned medium (5 ml) samples can then be pre-cleared e.g., using non-immune rabbit sera and Protein A-Sepharose. Pre-cleared supernatants are immunoprecipitated using e.g. a monospecific rabbit anti-$AP_{1-28}$ antibody (rpAb1–28) and Protein A-Sepharose. The samples can then be centrifuged (1000×g) and the supernatants discarded. Aβ immunoprecipitates can be solubilized and separated on SDS-PAGE where the separated proteins on the gels can be transferred to nitrocellulose (Hybond) and western immunoblotted using a monoclonal antibody, e.g., 6E10 (Senetek, Maryland Heights, Mo., ascites fluid diluted 1:3000). Proteins binding Aβ-antibodies can be identified using biotin-conjugated goat-anti-mouse IgG (Sigma, St. Louis, Mo., 1:1000) and streptavidin-horseradish peroxidase conjugate (1:1000, Amersham, Arlington Heights, Ill.). The peroxidase activity may be visualized e.g. using chemiluminescence (Amersham ECL kit).

Compound toxicity may be assessed e.g. using a LIVE/DEAβ EukoLight™ Viability/Cytotoxicity assay (Molecular Probes, Inc., Eugene, Oreg.) according to manufacturer recommended protocols.

Drug Treatment Studies In Vivo: For in vivo studies, APP-transgenic mice may be dosed, (e.g., subcutaneously, or, orally), with vehicle, or one or more of the instant compounds (e.g., at 10, 50, 100 or 200 μmoles/kg; with about 8–9 animals per group per timepoint). Blood and brain tissues may be collected at different times after injection. Samples are subject to ELISA assay, i.e., for analysis of levels of $Aβ_{1-40}$ in plasma or in CHAPS extracted brain tissues. Immunoprecipitation (with 26D6 monoclonal antibody and anti-mouse IgG or Protein A), western blotting and gel scanning densitometry may be used to confirm Aβ fragment levels in tissues and plasma.

As will be recognized by those skilled in the art, the various embodiments described herein are provided by way of illustration and not limitation; various modifications and substitutions may be made thereto without departing from the spirit and scope of the invention. Such modifications and substitutions are contemplated as within the scope of the following claims.

What is claimed is:

1. A cysteine protease inhibitor compound represented by FORMULA I or II:

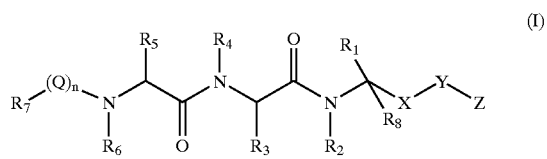

(I)

-continued

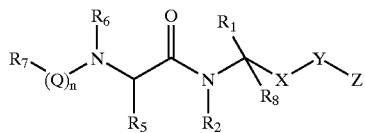

(II)

or a salt, isostere, or stereoisomer thereof, wherein:

$R_1$ is a W-substituted or unsubstituted lower alkenyl or a lower alkynyl, wherein said W-substituent is a halo, a hydroxy, an alkyl, an aryl, a heterocycle, a heteroaryl, an alkoxy, an aminosulfonyl, an alkylcarbonyl, an arylcarbonyl, a heteroarylcarbonyl, a heterocyclecarbonyl, a nitro, a haloalkyl, an amino or aminocarbonyl;

X is —CH=CH—(CH=CH)$_k$—(CH$_2$)$_j$ or —CH$_2$CH$_2$—(CH$_2$)$_b$, wherein k is an integer selected from 0 to 9, j is an integer selected from 0 to 4, b is an integer selected from 3 to 6;

Y is S, SO, SO$_2$, NR$_{20}$, —N(O)(R$_{20}$), —PR$_{20}$, —P(O)(R$_{20}$)—, —P(O)O— or —P(O)(OR$_{20}$)O, wherein R$_{20}$ is a hydrogen atom, an alkyl, or an aryl;

Z is —(CH$_2$)$_i$—A, wherein i is an integer selected from 0 to 4 and A is an L, substituted or unsubstituted heterocycle, a heteroaryl or an aryl, and further, wherein said L-substituent is a halogen, a lower alkyl, a lower alkenyl, a lower alkynyl, an alkoxy, an aryloxy, a hydroxy, a haloalkyl, a trifluoromethyl, a cyano, a nitro, a nitrile, an alkylthio, a phenyl, or an —NR$_{30}$R$_{31}$ group and wherein R$_{30}$ and R$_{31}$ each independently is H, alkyl, hydroxy or halo lower alkyl;

$R_2$, $R_3$, $R_4$, $R_5$, $R_6$, $R_7$, $R_8$, Q, and n are each selected according to a group selected from among groups (i), (ii), (iii), (iv), (v), (vi) and (vii) as follows:

(i) $R_3$ and $R_5$ each independently is a side chain of a naturally occurring α-amino acid, a hydrogen atom, an alkyl, an alkenyl, an alkynyl, an aryl, an aralkyl, an aralkenyl, an aralkynyl, a heteroaryl, a heteroaralkyl, a heteroaralkenyl, a heteroaralkynyl, an L-substituted aryl, an L-substituted aralkyl, an L-substituted aralkenyl, an L-substituted aralkynyl, an M-substituted heteroaryl, an M-substituted heteroaralkyl, an M-substituted heteroaralkenyl or an M-substituted heteroaralkynyl, wherein M is a lower alkyl or a halo lower alkyl;

$R_2$, $R_4$, $R_6$, and $R_8$ each independently is a hydrogen atom, a lower alkyl, a cycloalkyl or a cycloalkylalkyl;

$R_7$ is a C$_{1-6}$ alkyl, an R$_A$R$_B$CH, an aryl, an alkenyl, an alkynyl, a 9-fluorenyl, an aralkyl, an aralkenyl, an aralkynyl, a monocylic or a bicyclic heterocycle or a monocyclic or a bicyclic aryl, heteroaryl or arylheteroaryl, wherein said aryl, said heterocycle and said heteroaryl groups are optionally substituted with L;

Q is —C(O)—, —O—C(O)—, —S(O)2— or —HN—C(O)—;

n is zero or the integer 1;

$R_A$ is —(T)$_m$—(D)$_m$—R$_3$, wherein T is O or NH, D is C$_{1-4}$ alkyl or C$_{2-4}$ alkenyl, and m is zero or the integer 1, and $R_B$ is a substituent selected as set forth for R$_3$ and R$_5$; or alternatively, (ii) Q, $R_2$, $R_5$ and $R_8$ each independently is as set forth in (i);

$R_3$ and $R_4$ each independently is as recited in (i) or (iv); n is zero; and $R_6$ and $R_7$ together with the atoms to which each is attached form a 3–10 membered heterocyclic moiety containing 1–5 heteroatoms, wherein said moiety is optionally substituted with L; or alternatively, (iii) $R_2$, $R_3$, $R_4$, $R_5$ and $R_8$ each independently is as set forth in (i);

Q is —C(O)—;

n is 1; and $R_6$ and $R_7$ each independently is a substituted or unsubstituted carbonyl (—(C=O)—), phenylene, heteroatom, lower alkylene, or lower alkylene linked to a heteroatom, wherein said substituent is L and also wherein $R_6$ and $R_7$ together with the atoms to which they are attached form a cyclic or a bicyclic moiety, further wherein when $R_6$ and $R_7$ are both carbonyl at least one is substituted; or alternatively, (iv) $R_2$, $R_5$, $R_6$, $R_7$, $R_8$ and Q each independently is as set forth in any of (i)–(iii) or (v–vii), and n is zero or 1;

$R_3$ and $R_4$ each independently is a) a heteroatom, b) a substituted or unsubstituted lower alkylene, c) lower alkylene linked to a heteroatom, wherein said substituent is L, or d) $R_3$ and $R_4$ together with the atoms to which they are attached form a heterocyclic moiety; or alternatively, (v) $R_2$, $R_7$, $R_8$, Q each independently is as set forth in (i), and n is zero or 1;

$R_3$ and $R_4$ each independently is as set forth in either of (i) or (iv);

$R_5$ and $R_6$ each independently is a heteroatom or a substituted or unsubstituted lower alkylene or a lower alkylene linked to a heteroatom, wherein said substituent is L and also wherein $R_5$ and $R_6$ together with the atoms to which they are attached form a heterocyclic moiety; or alternatively, (vi) Q, $R_2$, $R_6$ and $R_8$ each independently is as set forth in (i), $R_3$ and $R_4$ each independently is as set forth in either of (i) or (iv);

n is zero; and $R_5$ and $R_7$ each independently is a heteroatom or a substituted or unsubstituted lower alkylene or lower alkylene linked to a heteroatom, wherein said substituent is L and also wherein $R_5$ and $R_7$ together with the atoms to which they are attached form a heterocyclic moiety; or alternatively, (vii) Q, $R_2$, $R_5$ and $R_6$ each independently is as set forth in (i);

$R_3$ and $R_4$ each independently is as set forth in either of (i) or (iv);

n is 0;

$R_6$ and $R_7$ each independently is a heteroatom or a substituted or unsubstituted lower alkylene or lower alkylene linked to a heteroatom, wherein said substituent is L and also wherein $R_6$ and $R_7$ together with the atoms to which each is attached form a 6–12 membered bicyclic heterocyclic or heteroaryl moiety.

2. The cysteine protease inhibitor compound of claim 1, wherein:

$R_2$, $R_3$, $R_4$, $R_5$, $R_6$, $R_7$, $R_8$s, Q in said groups (i)–(vii) are further limited as follows:

(i) wherein when either of $R_3$ or $R_5$ is an alkyl, each independently is a lower alkyl; when $R_3$ or $R_5$ is an alkenyl, each independently is a C$_{2-10}$ alkenyl; when $R_3$ or $R_5$ is an alkynyl each independently is a C$_{2-6}$ alkynyl; wherein said M constituent is a $C_{1-4}$ alkyl or a trifluoromethyl; when $R_2$, $R_4$, $R_6$, or $R_8$ is an alkyl, each independently is a $C_{1-4}$ alkyl; when $R_2$, $R_4$, $R_6$, or $R_8$ is an aryl, each independently is an L-substituted aryl; when $R_2$, $R_4$, $R_6$, or $R_8$ is a heterocycle each independently is an L-substituted heterocycle; when $R_2$, $R_4$, $R_6$, or $R_8$ is a heteroaryl, each independently is an L-substituted heteroaryl;

(ii) wherein $R_6$ and $R_7$ each independently is a morpholino, a thiomorpholino, a pyrrolidinyl or a 4-hydroxypyrrolidinyl;

(iii) wherein $R_6$ and $R_7$ each independently is a succinimidyl, a phthalimidyl or a maleimidyl;

(iv) $R_3$ and $R_4$ each independently is a morpholino, a thiomorpholino, a pyrrolidinyl or a 4-hydroxypyrrolidinyl; or alternatively, (v) $R_5$ and $R_6$ each independently is a morpholino, a thiomorpholino, a pyrrolidinyl or a 4-hydroxypyrrolidinyl;

(vi) $R_5$ and $R_7$ each independently is a morpholino, a thiomorpholino, a pyrrolidinyl or a 4-hydroxypyrrolidinyl; or alternatively, (vii) $R_6$ and $R_7$ each independently is 1,2,3,4-tetrahydroisoquinolinyl.

3. The cysteine protease inhibitor compound of claim 1, wherein k and j are 0 and b is 3 or 4.

4. The cysteine protease inhibitor compound of claim 1, wherein X is —CH=CH—.

5. The cysteine protease inhibitor compound of claim 1, wherein $R_1$ is a lower alkenyl.

6. The cysteine protease inhibitor compound of claim 1, wherein Y is SO, $SO_2$, —N(O)($R_{20}$), —P(O)($R_{20}$)— or —P(O)($OR_{20}$)—.

7. The cysteine protease inhibitor compound of claim 1, wherein Z is an L-substituted or unsubstituted phenyl, pyridyl, pyrazinyl, thienyl, furyl, pyrrolyl, imidazolyl or pyrimidinyl.

8. The cysteine protease inhibitor compound of claim 1, wherein Y is $SO_2$.

9. The cysteine protease inhibitor compound of claim 1, wherein

X is —CH=CH— and wherein

Y is not $NR_{20}$ and

A is an L-substituted or unsubstituted phenyl, pyridyl, pyrazinyl, thienyl, furyl, pyrrolyl, imidazolyl or pyrimidinyl, wherein said L is not aryloxy.

10. The cysteine protease inhibitor compound of claim 9, with the further provisos in said groups (i)–(vii) as follows:

(i) when $R_3$ or $R_5$ is an alkenyl or an alkynyl, each independently is a $C_{2-10}$ alkenyl or a $C_{2-6}$ alkynyl, and M is a $C_{1-4}$ alkyl or a trifluoromethyl;

(ii) when $R_2$, $R_4$, $R_6$, or $R_8$ is a lower alkyl, each independently is a $C_{1-4}$ alkyl and when $R_6$ and $R_7$ together with the atoms to which each is attached form a heterocyclic moiety, said moiety is a morpholino, a thiomorpholino, pyrrolidinyl or a 4-hydroxypyrrolidinyl;

(iii) when $R^6$ and $R_7$ together with the atoms to which they are attached form a cyclic or bicyclic moiety, said moiety is a succinimidyl, a phthalimidyl or a maleimnidyl;

(iv) when $R_3$ and $R_4$ together with the atoms to which they are attached form a heterocyclic moiety, said moiety comprises a morpholino, a thiomorpholino, pyrrolidinyl or a 4-hydroxypyrrolidinyl;

(v) when $R_5$ and $R_6$ together with the atoms to which they are attached form a heterocyclic moiety, said moiety is a morpholino, a thiomorpholino, pyrrolidinyl or a 4-hydroxypyrrolidinyl;

(vi) when $R_5$ and $R_7$ together with the atoms to which they are attached form a heterocyclic moiety, said moiety is a morpholino, a thiomorpholino, pyrrolidinyl or a 4-hydroxypyrrolidinyl; and (vii) when $R_6$ and $R_7$ together with the atoms to which they are attached form a heteroaryl moiety, said moiety is a 1,2,3,4-tetrahydro isoquinolinyl.

11. The cysteine protease inhibitor compound of claim 9, wherein: $R_1$ is an unsubstituted lower alkenyl or lower alkynyl and Y is SO or $SO_2$.

12. The cysteine protease inhibitor compound of claim 11, wherein $R_1$ is an unsubstituted lower alkenyl and Y comprises $SO_2$.

13. The cysteine protease inhibitor compound of claim 12, wherein: $R_1$ is 2-methylpropenyl or 2-butenyl; $R_2$, $R_4$, $R_6$ and $R_8$ each independently is a $C_{1-4}$ alkyl, a lower cycloalkyl or a lower cycloalkylalkyl; $R_3$ and $R_5$ each independently is a hydrogen atom, a $C_{1-4}$ alkyl, a alkylthio-alkyl, an aryl, an aralkyl, a heteroaralkyl, a 1-aminobut-4-yl or an aminocarbonyl—$CH_2$-substituent; $R_7$ and (Q)n taken together is a acetyl, a benzyloxycarbonyl, an O-(3-chlorophenyl)-lactyl, a 9-fluorenylmethylcarbonyl, a Boc, 4-benzylpiperidinocarbonyl, a 4-benzylpiperazino-carbonyl or 1,2,3,4-tetrahydroisoquinolinylcarbonyl; and Z is an L-substituted or unsubstituted phenyl.

14. The cysteine protease inhibitor compound of claim 9, wherein $R_1$ is 2-methylpropenyl.

15. The cysteine protease inhibitor compound of claim 9, wherein: $R_1$ is 2-methylpropenyl; $R_2$, $R_4$, $R_6$ and $R_8$ each independently is a hydrogen atom, a cyclopropyl or a cyclopropyl-methyl; $R_3$ is isobutyl benzyl, (2-methylthio) ethyl or isopropyl; $R_5$ is an isopropyl or an isobutyl; $R_7$ and (Q)n taken together is benzyloxycarbonyl, 4-benzylpiperidinocarbonyl, 4-benzylpiperazinocarbonyl or 1,2,3,4-tetrahydro-isoquinolinylcarbonyl; Y is $SO_2$; and Z is a phenyl or a 4-(3-hydroxy-1-propynyl)phenyl.

16. The cysteine protease inhibitor compound of claim 1 selected from the group consisting of:

N-Cbz-L-ILu-L-Leu-L-Leuene phenyl vinyl sulfone;

N-Cbz-L-Leu-L-Leu-D-Leuene phenyl vinyl sulfone;

N-(THIQ-carbonyl)-L-Leu-L-Lu-D-Leuene phenyl vinyl sulfone;

N-(THIQ-carbonyl)-L-Leu-L-Leu-L-Leuene phenyl vinyl sulfone;

N-(THIQ-carbonyl)-L-Val-L-Met-Leuene phenyl vinyl sulfone;

N-(THIQ-carbonyl)-L-Val-L-Met-D-leuene phenyl vinyl sulfone;

N-(THIQ-carbonyl)-L-Val-L-Leu-L-Leuene phenyl vinyl sulfone;

N-(THIQ-carbonyl)-L-Val-L-Leu-D-Leuene phenyl vinyl sulfone;

N-(benzylpiperidinylcarbonyl)-L-Leu-L-Leu-L-Leuene phenyl vinyl sulfone;

N-(benzylpiperidinylcarbonyl)-L-Leu-L-Leu-D-Leuene phenyl vinyl sulfone;

N-(benzylpiperazinylcarbonyl)-L-Leu-L-Leu-L-Leuene phenyl vinyl sulfone; and

N-(benzylpiperazinylcarbonyl)-L-Leu-L-Leu-D-Leuene phenyl vinyl sulfone, wherein "THIQ" represents tetrahydroisoquinoline, "Cbz" represents carboxybenzyloxy, and "Leuene" represents 3-amino-5-methyl-1-hexene.

17. A composition comprising one or more cysteine protease inhibitor compounds of claim 1, or a pharmaceutically acceptable salt, isostere, mixture or stereoisomer thereof in an amount effective to inhibit a cysteine protease, together with a suitable carrier.

18. A composition comprising one or more cysteine protease inhibitor compounds of claim 9, or a pharmaceutically acceptable salt, isostere or stereoisomer thereof in an amount effective to inhibit a cysteine protease, together with a suitable carrier.

19. A mixture comprising two or more cysteine protease inhibitors according to claim 1.

* * * * *

UNITED STATES PATENT AND TRADEMARK OFFICE
CERTIFICATE OF CORRECTION

PATENT NO. : 6,617,426 B1  
DATED : September 9, 2003  
INVENTOR(S) : Benito Munoz, Kuman Srinivasan and Bowei Wang It is certified that error appears in the above-identified patent and that said Letters Patent is hereby corrected as shown below:

<u>Title page,</u>  
Add: -- [73] Assignee: Merck & Co., Inc., Rahway, NJ --

Signed and Sealed this

Fourth Day of November, 2003

JAMES E. ROGAN  
*Director of the United States Patent and Trademark Office*